United States Patent [19]

Althuis et al.

[11] 4,263,438

[45] Apr. 21, 1981

[54] 3-[2,4-(DISUBSTITUTED)-PHENYL]AZACY-CLOALKANONES AS ANALGESICS

[75] Inventors: Thomas H. Althuis, Groton; Charles A. Harbert, Waterford; Michael R. Johnson; Lawrence S. Melvin, Jr., both of Gales Ferry, all of Conn.

[73] Assignee: Pfizer Inc., New York, N.Y.

[21] Appl. No.: 419

[22] Filed: Jan. 2, 1979

Related U.S. Application Data

[62] Division of Ser. No. 832,869, Sep. 13, 1977, Pat. No. 4,147,872.

[51] Int. Cl.³ .......................................... C07D 211/74
[52] U.S. Cl. ................................ 546/216; 260/239 B; 260/239 BF; 260/326.47; 260/326.5 J; 546/194; 546/221; 546/275; 546/281
[58] Field of Search ............... 546/216, 221, 281, 275, 546/194; 260/239 B, 239 BF, 326.47, 326.5 J

[56] References Cited

U.S. PATENT DOCUMENTS

| | | | |
|---|---|---|---|
| 4,002,632 | 1/1977 | van der Burg | 546/216 X |
| 4,065,290 | 12/1977 | Taylor | 546/216 X |
| 4,193,926 | 3/1980 | Schmiechen et al. | 260/326.47 X |

*Primary Examiner*—Henry R. Jiles
*Assistant Examiner*—Richard A. Schwartz
*Attorney, Agent, or Firm*—Francis X. Murphy; Charles J. Knuth; Albert E. Frost

[57] ABSTRACT

Azacycloalkanes, and derivatives thereof, including unsaturated analogs, each of which has at the 3-position a 2-hydroxy-4-substituted phenyl group wherein the 4-position substituent is alkyl which can have an oxygen atom as part of the chain, or aralkyl which can have an oxygen atom as part of the alkyl chain, their use for pharmacological and medicinal purposes, intermediates therefor and processes for their preparation.

5 Claims, No Drawings

3-[2,4-(DISUBSTITUTED)-PHENYL]AZACYCLOALKANONES AS ANALGESICS

CROSS REFERENCE TO RELATED APPLICATION

This application is a division of application Ser. No. 832,869 filed Sept. 13, 1977, now U.S. Pat. No. 4,147,872, issued Apr. 3, 1979.

BACKGROUND OF THE INVENTION

1. Field of the Invention

This invention relates to certain azacycloalkanes and derivatives thereof, including unsaturated analogs, having from 4 to 7 carbon atoms in the azacycloalkyl ring and at the 3-position a 2-hydroxy-4-(Z-W-substituted)-phenyl group wherein Z is alkylene having from one to thirteen carbon atoms or $(alk_1)_m$—O—$(alk_2)_n$—wherein each of m and n is 0 or 1 and each of $(alk_1)$ and $(alk_2)$ is alkylene having from one to thirteen carbon atoms with the proviso the summation of carbon atoms in $(alk_1)$ plus $(alk_2)$ is not greater than thirteen and W is hydrogen, pyridyl, phenyl, fluorophenyl or chlorophenyl; derivatives thereof, intermediates therefor and processes for their preparation. The products are useful as CNS agents, especially as analgesics, tranquilizers, sedatives and antianxiety agents in mammals, including man, and/or as anticonvulsants, diuretics and antidiarrheal agents in mammals, including man.

2. Description of the Prior Art

Despite the current availability of a number of analgesic agents, the search for new and improved agents continues, thus pointing to the lack of an agent useful for the control of broad levels of pain and accompanied by a minimum of side-effects. The most commonly used agent, aspirin, is of no practical value for the control of severe pain and is known to exhibit various undesirable side-effects. Other analgesic agents such as d-propoxyphene, codeine, and morphine, possess addictive liability. The need for improved and potent analgesic agents is, therefore, evident.

More recently, great interest in cannabinol-type compounds as analgesic agents has been exhibited. (R. Mechoulam, Ed., "Marijuana. Chemistry, Pharmacology, Metabolism and Clinical Effects", Academic Press, New York, N.Y., 1973; Mechoulam, et al., Chemical Reviews, 76, 75–112 [1976]).

German Specification No. 2,621,535, published Nov. 25, 1976, describes 3-(3,4-dihydroxyphenyl)piperidines having dopaminergic and hypotensive activity. Also described in this specification are intermediates to said compounds, including N-benzyl-, 0-benzyl- or methoxy-derivatives, $\Delta^2$- and $\Delta^3$- derivatives and 3-(3,4-dibenzyloxyphenyl)-3-hydroxy-N-benzylpiperidine. N-alkyl, alkenyl and aralkyl derivatives of said compounds having the same utility are described in German Specification No. 2,621,536, published Nov. 25, 1976.

SUMMARY OF THE INVENTION

It has now been found that certain azacycloalkanes and derivatives thereof, including unsaturated analogs, having at the 3-position a 2-hydroxy-4-(substituted)phenyl group (formulae I-II below) are effective as CNS agents, especially as analgesics, tranquilizers, sedatives and antianxiety agents in mammals, including humans, and/or as anticonvulsants, diuretics and antidiarrheal agents in mammals, including man. Also included in this invention are various derivatives of said compounds which are useful as dosage forms of the compounds, intermediates for compounds having formulae I and II, and methods for their preparation. The compounds have the formulae:

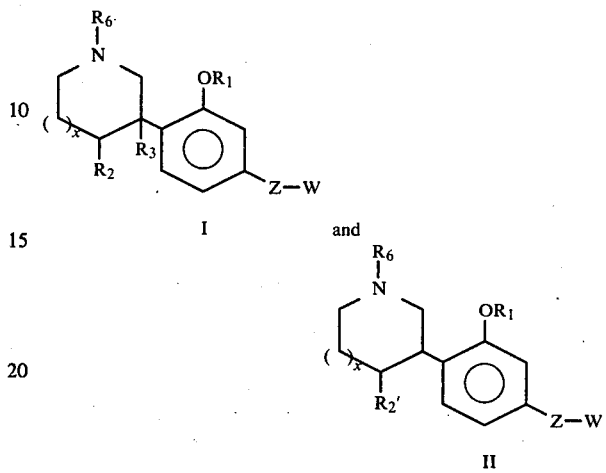

(in which stereochemistry is not represented);

wherein $R_1$ is selected from the group consisting of hydrogen, alkanoyl having from one to five carbon atoms, benzyl, —P(O)(OH)$_2$ and the sodium and potassium salts thereof, —CO(CH$_2$)$_2$—COOH and the sodium and potassium salts thereof, and —CO—(CH$_2$)$_p$—NR$_4$R$_5$ wherein p is an integer from 1 to 4, each of R$_4$ and R$_5$ when taken individually is selected from the group consisting of hydrogen and alkyl having from one to four carbon atoms, R$_4$ and R$_5$ when taken together with the nitrogen to which they are attached form a 5- or 6-membered heterocyclic ring selected from the group consisting of piperidino, pyrrolo, pyrrolidino, morpholino and N-alkylpiperazino having from one to four carbon atoms in the alkyl group;

$R_2$ is selected from the group consisting of hydroxy and $R_2'$ wherein $R_2'$ is selected from the group consisting of hydrogen, alkyl having from one to six carbon atoms, phenyl and phenylalkyl having from one to four carbon atoms in the alkyl group;

$R_3$ is selected from the group consisting of hydrogen and hydroxy, with the proviso that only one of $R_2$ and $R_3$ is hydroxy;

$R_6$ is selected from the group consisting of hydrogen, alkenyl having from two to six carbon atoms, alkynyl having from two to six carbon atoms, and $R_6'$ wherein $R_6'$ is selected from the group consisting of alkyl having from one to six carbon atoms, cycloalkylmethyl having from three to six carbon atoms in the cycloalkyl group, phenylalkyl having from one to four carbon atoms in the alkyl group, 2-furfuryl, 2-tetrahydrofurfuryl, 2-thienylmethyl and 2-tetrahydrothienylmethyl;

x is 0 or an integer from 1 to 3;

Z is selected from the group consisting of (a) alkylene having from one to thirteen carbon atoms; (b) $-(alk_1)_m$-O-$(alk_2)_n$- wherein each of $(alk_1)$ and $(alk_2)$ is alkylene having from one to thirteen carbon atoms, with the proviso that the summation of carbon atoms in $(alk_1)$ plus $(alk_2)$ is not greater than thirteen; each of m and n is 0 or 1; and W is selected from the group consisting of hydrogen, pyridyl,

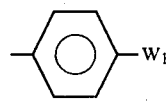

wherein $W_1$ is selected from the group consisting of hydrogen, fluoro and chloro.

Also included in this invention are the pharmaceutically acceptable acid addition salts of those compounds of formulae I and II which contain a basic group. In compounds having two or more basic groups present, such as those wherein the W variable is pyridyl and/or $OR_1$ represents a basic ester moiety, polyacid addition salts are, of course, possible. Representative of such pharmaceutically acceptable acid addition salts are the mineral acid salts such as the hydrochloride, hydrobromide, sulfate, phosphate, nitrate; organic acid salts such as the citrate, acetate, sulfosalicylate, tartrate, glycolate, malate, malonate, maleate, pamoate, salicylate, stearate, phthalate, succinate, gluconate, 2-hydroxy-3-naphthoate, lactate, mandelate and methane sulfonate.

Compounds of formulae I and II contain asymmetric centers at the 3- and the 4-positions in the azacycloalkyl moiety and may, of course, contain additional asymmetric centers in the 4-position substituent (-Z-W) of the benzenoid ring and in the $R_6$ substituent. For convenience, the above formulae depict the racemic compounds. However, the above formulae are considered to be generic to and embracive of the racemic modifications of the compounds of this invention, the diastereomeric mixtures, the pure enantiomers and diastereomers thereof. The utility of the racemic mixture, the diastereomeric mixture as well as of the pure enantiomers and diastereomers is determined by the biological evaluation procedures described below.

In addition to the above formulae, various intermediates useful in the preparation of compounds of formulae I and II are also included in this invention. The intermediates have formulae III and IV below:

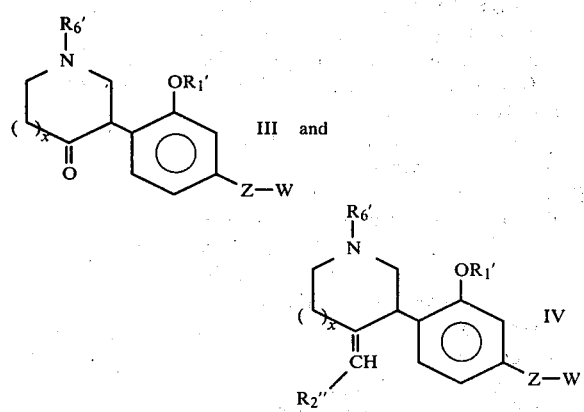

wherein $R_1'$ is selected from the group consisting of hydrogen and benzyl; and $R_6'$, Z, W and x are as previously defined; and $R_2''$ is selected from the group consisting of hydrogen, alkyl having from one to five carbon atoms, phenyl and phenylalkyl having from one to three carbon atoms in the alkyl group.

Favored because of their greater biological activity relative to that of other compounds described herein are compounds of formulae I and II wherein $R_1$ is hydrogen or alkanoyl; $R_2$ is hydrogen or alkyl; and Z and W have the values shown below.

| Z | m | n | W |
|---|---|---|---|
| alkylene having from 5 to 10 carbon atoms | — | — | H |
| alkylene having from 2 to 6 carbon atoms | — | — | ―⟨O⟩―$W_1$, pyridyl |
| $(alk_1)_m$―O―$(alk_2)_n$ | 0 | 1 | ―⟨O⟩―$W_1$, pyridyl |
| $(alk_1)_m$―O―$(alk_2)_n$ | 1 | 0 | ―⟨O⟩―$W_1$, pyridyl |

Preferred compounds of formulae I and II are those favored compounds wherein:
each of $R_1$ and $R_2$ is hydrogen;
x = 1;
$R_6$ is allyl and propargyl;
Z is ―$C(CH_3)_2(CH_2)_6$ and W is hydrogen
or Z is ―$OCH(CH_3)(CH_2)_3$ and W is phenyl.

DETAILED DESCRIPTION OF THE INVENTION

The compounds of this invention having formula I wherein $R_3$ is hydroxy are prepared from the appropriate 2-bromo 5-(Z-W substituted)phenol by a series of reactions which comprises as first step protection of the phenolic hydroxy group. Suitable protecting groups are those which do not interfere with subsequent reactions, and which can be removed under conditions which do not cause undesired reactions, at other sites of said compounds or of products produced therefrom. Representative of such protective groups are methyl, ethyl, benzyl or substituted benzyl wherein the substituent is, for example, alkyl having from one to four carbon atoms, halo (Cl, Br, F, I) and alkoxy having from one to four carbon atoms.

The exact chemical structure of the protecting group is not critical to this invention since its importance resides in its ability to perform in the manner described above. The selection and identification of appropriate protecting groups can easily and readily be made by one skilled in the art. The suitability and effectiveness of a group as a hydroxy protecting group are determined by employing such a group in the herein-illustrated reaction sequences. It should, therefore, be a group which is easily removed to regenerate the hydroxy groups. Methyl is a favored protecting group since it is easily removed by treatment with pyridine hydrochloride. The benzyl group is a preferred protecting group since it can be removed by catalytic hydrogenolysis or acid hydrolysis.

The protected 2-bromo-5-(Z-W substituted)phenol is then subjected to the Grignard reaction in a reaction-inert solvent with the appropriate azacycloalkan-3-one (upper portion of Scheme A). Suitable reaction-inert solvents are cyclic and acyclic ethers such as, for example, tetrahydrofuran, dioxane and dimethyl ether of ethylene glycol.

The Grignard reagent is formed in known manner, as, for example, by refluxing a mixture of one molar proportion of the bromo reactant and two molar proportions of magnesium in a reaction-inert solvent, e.g., tetrahydrofuran. The resulting mixture is then cooled to about 0° C. to −20° C. The appropriate azacycloalkan- 3-one is then added at a temperature of from about 0° C. to −20° C.

The product of the Grignard reaction (formula I, $R_1$=benzyl, $R_3$=OH) is then treated with an appropriate reagent to remove the protecting group. If desired, the benzyl group on the phenolic hydroxy group and, if present, that on the nitrogen of the azacycloalkyl moiety, are conveniently removed by catalytic hydrogenation over palladium-on-carbon. Alternatively, the phenolic benzyl group can be removed by acid hydrolysis using, for example, trifluoroacetic acid, if retention of the N-benzyl group is desired. A further alternative when retention of the N-benzyl group is desired comprises using an alkyl ether of the phenolic hydroxy group, preferably a methyl or ethyl ether as reactant in the Grignard reaction. Subsequent treatment of the Grignard reaction product with, for example, pyridine hydrochloride, removes the alkyl protecting group and retains the N-benzyl group.

Compounds of formula I wherein $R_3$ is hydroxy are dehydrated by treatment with a strong acid, such as hydrochloric, hydrobromic, sulfuric, hydrofluoric or p-toluenesulfonic acid to produce formula II compounds. Other dehydrating agents such as thionyl chloride, pyridine, phosphorous oxychloride, and tosyl or mesyl chloride —$SO_2$ plus an acid acceptor can, of course, be used. Catalytic hydrogenation of said compounds gives formula I compounds. Of course, if either of $R_1$ or $R_6$ of the formula II compound is benzyl, it is removed by this catalytic hydrogenation step.

Since the compounds of this invention can have a group $R_6'$ ($R_6$=$R_6'$) on the nitrogen of the azacycloalkyl moiety (formulae I-IV), it will frequently not be desirable or necessary to remove the nitrogen protecting group $R_6'$ except, of course, when $R_6$ is to be hydrogen, alkenyl or alkynyl. The preferred nitrogen protecting group when removal of said group is necessary is benzyl since it is readily removed by catalytic hydrogenation over palladium-on-carbon. Debenzylation is desirably carried out on the product of the Grignard reaction to provide the corresponding 3-hydroxy-3-[4-(Z-W)-2-hydroxyphenyl]azacycloalkane which is subsequently dehydrated to a formula II compound wherein $R_6$=$R_1$=H. Catalytic hydrogenation (Pd/C) then gives a compound of formula I. Alkylation or aralkylation of the formula I or II compound with $R_6$Cl or $R_6$Br then provides the desired substitution on the azacycloalkyl group. The reaction is conducted in a solvent, e.g. alkanols such as ethanol, n-butanol, 1-hexanol, at a temperature of from about 50° C. to the reflux temperature of the solvent. An acid acceptor, inorganic or organic, is used to bind the by-product acid formed. Suitable bases are alkali metal carbonates and hydroxides, pyridine, triethylamine, N-methylmorpholine.

A favored procedure for introducing substituents on the nitrogen of the azacycloalkyl ring is reductive alkylation (or aralkylation) using the appropriate aldehyde in the presence of a reducing agent. When the azacycloalkyl compound is of formula I, the reducing agent can be molecular hydrogen and a catalyst, e.g. Pd/C, active metals and acids or metal hydrides. When the azacycloalkyl compound is of formula II, i.e. an azacycloalkenyl, a metal hydride is used to avoid reducing the azacycloalkenyl group. Also, when the substituent is an alkenyl or alkynyl group, a metal hydride is used as reducing agent. Preferred as metal reducing agent is sodium cyanoborohydride. The reaction is conducted in a reaction-inert solvent such as acetonitrile, tetrahydrofuran, alcohols having from one to four carbon atoms, ethylene or propylene glycol, dioxane, benzene and toluene; and at a temperature of from about 10° C. to about 50° C. The reaction is carried out at about a neutral pH by addition of an acid such as acetic acid.

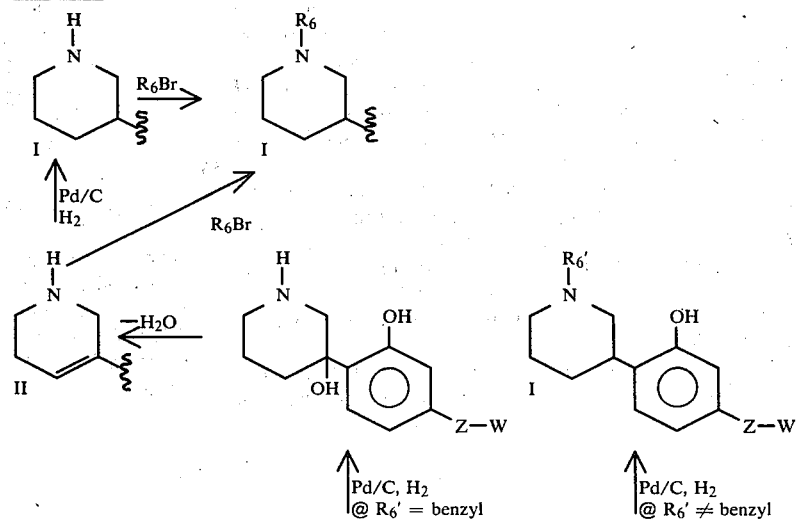

Scheme A

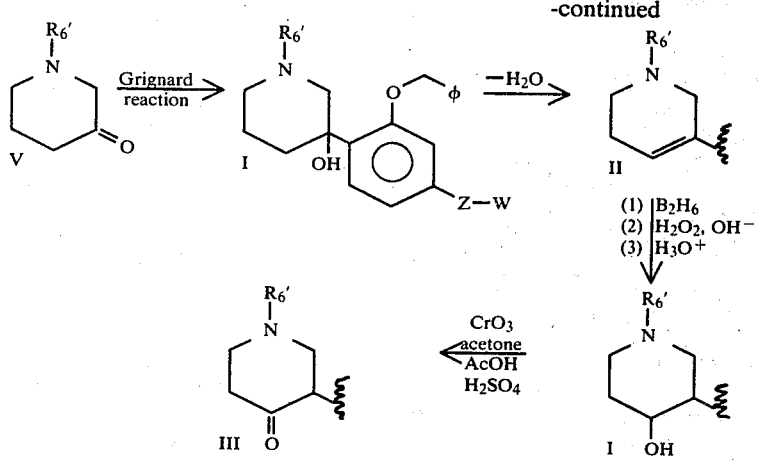

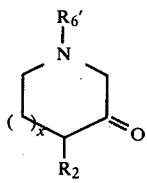

Appropriate azacycloalkan-3-ones are those having the formula wherein $R_6'$ is a nitrogen protecting group. The function of such a group is to prevent undesired reactions from occurring at the nitrogen atom and which, when the desired reaction is completed, can, if desired or necessary, be removed under conditions which do not cause undesired reactions at other sites of the compounds or products produced therefrom. Representative of such groups are phenylalkyl having from one to four carbon atoms in the alkyl group, alkyl having from one to six carbon atoms, cycloalkylmethyl having from three to six carbon atoms in the alkyl group, furfuryl, tetrahydrofurfuryl, 2-thienylmethyl and 2-tetrahydrothienylmethyl.

The general non-availability of compounds of formula V gives rise to a situation where protection of said formula V reactant as its benzyl derivative frequently affords the most convenient route to compounds of formulae I-II wherein $R_6$ is other than hydrogen. Debenzylation of the formulae I-II compounds wherein $R_6$ is benzyl and subsequent alkylation of the <NH group thereof with $R_6Cl$ or $R_6Br$ according to known procedures affords the desired product wherein $R_6$ is other than hydrogen or benzyl.

Further, since benzyl is a favored protecting group for the phenolic hydroxy group, protection of both the phenolic hydroxy and the nitrogen of the azacycloalkan-3-one reactants by benzylation simplifies, by virtue of a single reaction, regeneration of the phenolic hydroxy and <NH groups in formulae I-II compounds wherein $R_6$ is hydrogen.

In the lower portion of Scheme A, the 1,2,5,6-tetrahydropyridine is subjected to hydroboration and then oxidation to produce a 4-piperidinol which, upon oxidation by means of chromium trioxide in acetone solution in the presence of acetic acid and sulfuric acid at a temperature of from about $-10°$ C. to about 20° C., affords a 4-piperidone of formula III.

Preparation of 4-$R_2'$-substituted compounds of formulae I or II can be accomplished in any of several ways. One method (Scheme B) comprises reacting a compound of formula III with an appropriate Grignard reactant $R_2'MgBr$ in a suitable reaction-inert solvent under conditions such as are described above to produce a 4-$R_2'$-4-piperidinol which is dehydrated using an agent such as thionyl chloride-pyridine to a 4-$R_2'$-substituted-1,2,5,6-tetrahydropyridine. Catalytic hydrogenation then gives a saturated compound of formula I.

Scheme B

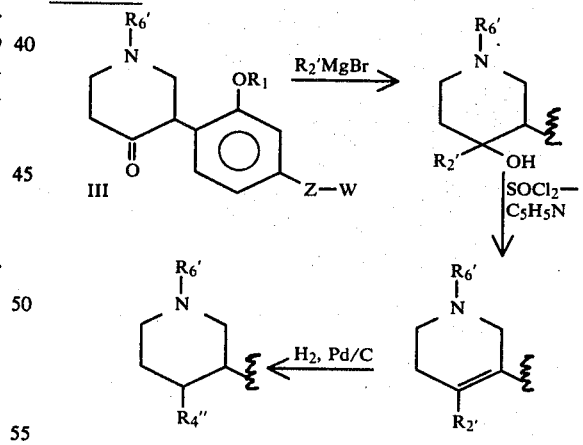

A further method comprises reacting a formula III compound with an appropriate triphenyl-$R_2''$-phosphorane in dimethylsulfoxide (Scheme C). Appropriate triphenyl-$R_2''$-phosphoranes are those wherein $R_2''$ has all values listed above with respect to formula IV. The 4-alkylidene or aralkylidene compound thus produced (formula IV) is then catalytically hydrogenated (Pd/C). Simultaneous debenzylation also occurs.

Scheme C

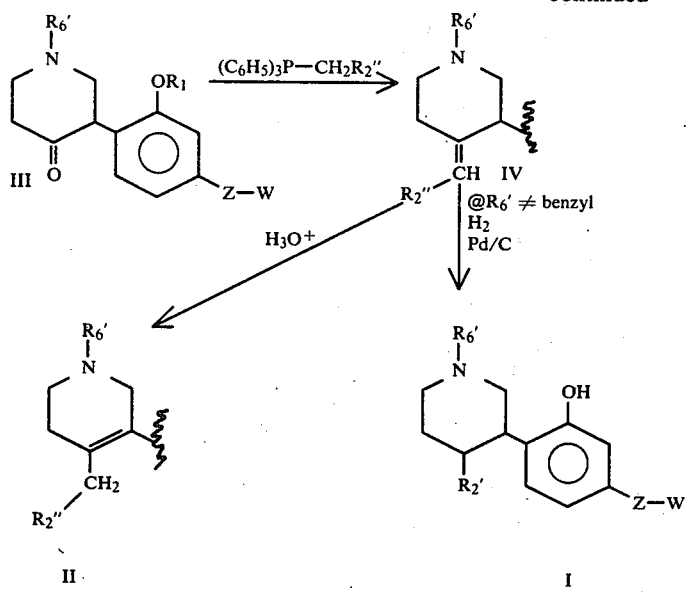

Acid treatment of IV causes isomerization to a compound of formula II.

A still further method, and one which is favored since it achieves introduction of the $R_2'$ substituent at an early stage, is that of Scheme D. In this scheme, a protected ($R_6'$) substituted 4-piperidone is reacted with an appropriate Grignard reactant to give the corresponding 4-$R_2'$-4-piperidinol which is dehydrated according to the procedure of Scheme B. Hydroboration and subsequent oxidation of the protected 4-$R_2'$-1,2,5,6-tetrahydropyridine produces a 4-$R_2'$-3-piperidinol which is then oxidized with chromium trioxide according to the procedure described above in Scheme A to give a protected 4-$R_2'$-3-piperidone of formula V. Subjection of this compound to the reactions outlined in Scheme A then produces compounds of formulae II and I.

Scheme D serves adequately for preparation of $R_2'$-substituted products except those wherein $R_2'$ is benzyl. The benzyl group is conveniently introduced via the procedure of Scheme C.

Scheme D

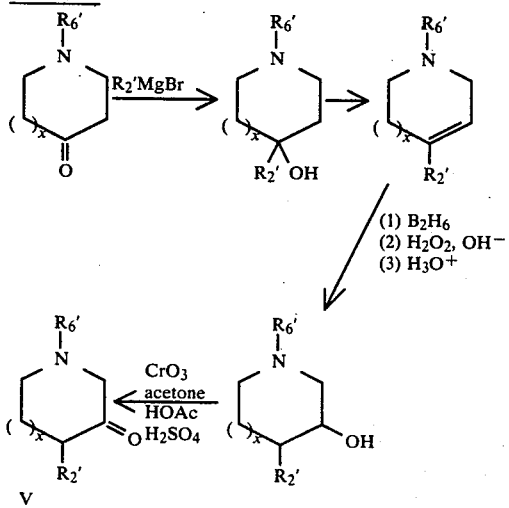

The procedure described by Beckett et al., *J. Med. Pharm. Chem.*, 1, 37–58 (1959) affords a general procedure for preparation of 1-($R_6'$-substituted)-4-piperidone reactants of Scheme D. The procedure comprises reacting an appropriate amine $R_6'$-$NH_2$ with excess ethyl acrylate in a suitable solvent such as ethanol to produce the corresponding N-di-(2-carbethoxyethyl)-$R_6'$-substituted amine. The di-ester is then cyclized via the Dieckmann reaction using metallic sodium as base in a reaction inert solvent such as xylene to produce the corresponding 1-$R_6'$-substituted-3-carbethoxy-4-piperidone. Decarboxylation of this product is accomplished by refluxing with aqueous hydrochloric acid to produce the desired 1-$R_6'$-substituted-4-piperidone. The 4-piperidone thus obtained is converted to a 3-piperidone via the method of Scheme D.

Prill et al., *J. Am. Chem. Soc.*, 55, 1233-41 (1933), describe a general procedure for preparation of azacycloalkanones by which the keto group can, by judicious choice of reactants, be introduced at the 3- or the 4-position. The procedure comprises reacting the appropriate N-substituted amino acid ethyl ester with the appropriate ethyl ω-bromoalkanoate to form a diester which is then cyclized by means of sodium ethoxide to give a 1-(substituted)-azacycloalkan-3(or 4)-one.

The 2-bromo-5-(Z-W substituted) phenol reactants are prepared by bromination of the appropriate 3-(Z-W substituted) phenol according to standard procedures as, for example, by treatment with bromine in carbon tetrachloride at a temperature of from about 20°–30° C. The necessary 3-(Z-W substituted) phenols, if not known compounds, are prepared by procedures illustrated herein. A convenient method for preparing such reactants wherein the Z moiety is alkylene or ($alk_1$)-O-($alk_2$)$_n$- comprises the Wittig reaction on an appropriate aldehyde such as 2-(3-hydroxyphenyl)-2-methyl propionaldehyde, the hydroxy group of which is protected by benzyl ether formation. The said aldehyde is then treated with the appropriate alkyltriphenylphosphonium bromide, the alkyl group of which extends the propionaldehyde group to the desired length. In a typical procedure, the aldehyde reactant is added to a slurry of dimsyl sodium and alkyl triphenylphosphonium bromide in dimethyl sulfoxide at a temperature below 30° C., e.g. from about 10° to 30° C. When reaction is complete, the alkene substituted protected phenol is recovered by known methods. Hydrogenation of the alkene over palladium-on-carbon then affords the desired 3-(Z-W substituted)phenol. Judicious choice of the starting (3-hydroxyphenyl)-substituted aldehyde and alkyl triphenylphosphonium bromide reactants affords the required 3-(Z-W-substituted)phenol reactants.

A further procedure for making 3-(Z-W substituted) phenols wherein Z is alkylene or (alk$_1$)-O-(alk$_2$)$_n$- comprises the Wittig reaction on an appropriate phenolic aldehyde or ketone, e.g., 3-hydroxybenzaldehyde or a (3-hydroxyphenyl)alkyl ketone, in which the phenolic hydroxy group is protected as by conversion to the benzyl, methyl or ethyl ether. By choice of appropriate reactants, compounds having straight or branched alkylene groups (Z) can be produced. When a ketone, e.g., 3-hydroxyacetophenone is used as reactant, compounds wherein Z has a methyl group on the carbon atom adjacent to the phenyl group are obtained.

Substitution of a methyl or ethyl group at other sites, e.g., the β-carbon atom of the alkylene group, is achieved by choice of the appropriate carboalkoxy alkylidene triphenylphosphorane, e.g., $(C_6H_5)_3P=C(R')-COOC_2H_5$. The unsaturated ester thus produced is reduced to the corresponding alcohol by reaction with lithium aluminum hydride, generally in the presence of a small amount of aluminum chloride. Alternatively, when the phenolic protecting group is other than benzyl (e.g. methyl), the alcohol is produced by catalytic reduction of the unsaturated ester using palladium-carbon, followed by treatment of the saturated ester thus produced with lithium aluminum hydride. Conversion of the alcohol thus produced to the corresponding tosylate or mesylate followed by alkylation of the tosylate or mesylate with an alkali metal salt of the appropriate HO-(alk$_2$)-W reactant, and finally removal of the protecting group affords the desired resorcinol 3-(Z-W substituted) phenol.

A variation of the above sequence comprises bromination of the alcohol rather than converting it to a tosylate or mesylate. Phosphorous tribromide is a convenient brominating agent. The bromo derivative is then reacted with the appropriate HO-(alk$_2$)-W in the presence of a suitable base (Williamson reaction).

The bromo compounds also serve as valuable intermediates for increasing the chain length of the alkylene moiety in the above sequence to give compounds wherein Z is -alkylene-W. The process comprises treating the bromo derivative with triphenyl phosphine to produce the corresponding triphenylphosphonium bromide. Reaction of the triphenylphosphonium bromide with the appropriate aldehyde or ketone in the presence of a base such as sodium hydride or n-butyl lithium affords an unsaturated derivative which is then catalytically hydrogenated to the corresponding saturated compound.

An alternative method for introducing an alkyl or aralkyl group into the aromatic nucleus, and specifically such a group wherein the carbon atom adjacent the aromatic nucleus is a tertiary carbon atom, comprises acid catalyzed electrophilic substitution of guaiacol with a tertiary alcohol in the presence of an acid, e.g methane sulfonic acid. The general procedure consists in reacting a mixture of methanesulfonic acid and equimolar amounts of guaiacol and tertiary alcohol at temperatures of from about 30° C. to about 80° C. until reaction is substantially complete. The product is isolated by pouring the reaction mixture onto ice followed by extraction with a suitable solvent such as methylene chloride. The 2-methoxy-4-alkyl phenol is then converted to the desired 3-alkyl phenol by removal of the phenolic hydroxy group. The process comprises converting the hydroxy group to a dialkyl phosphate group by reaction with a dialkyl chlorophosphonate, e.g. diethyl chlorophosphonate, or with diethyl phosphonate and triethylamine. Treatment of the dialkyl phosphate with lithium/ammonia followed by demethylation of the resulting alkylated methyl ether with boron tribromide or pyridine hydrochloride or other known demethylating agents affords the desired 3-alkylphenol.

Esters of compounds of formulae I and II wherein $R_1$ is alkanoyl or. $-CO-(CH_2)_pNR_4R_5$ are readily prepared by reacting formulae I and II compounds wherein $R_1$ is hydrogen with the appropriate alkanoic acid or acid of formula $HOOC-(CH_2)_p-NR_4R_5$ in the presence of a condensing agent such as dicyclohexylcarbodiimide. Alternatively, they are prepared by reaction of a formula I or II compound with the appropriate alkanoic acid chloride or anhydride, e.g., acetyl chloride or acetic anhydride, in the presence of a base such as pyridine.

Phosphate esters are prepared by treating the appropriate 1—R$_6$—[3—(4—Z-W)-2-hydroxyphenyl] azacycloalkane with potassium hydride followed by dibenzylphosphorochloridate. Catalytic hydrogenation of the dibenzylphosphate ester affords the desired phosphate ester. Cautious neutralization with sodium or potassium hydroxide provides the corresponding sodium or potassium salts.

The analgesic properties of the compounds of this invention are determined by tests using nociceptive stimuli.

TESTS USING THERMAL NOCICEPTIVE STIMULI (a) Mouse Hot Plate Analgesic Testing The method used is modified after Woolfe and MacDonald, *J. Pharmacol. Exp. Ther.*, 80, 300–307 (1944). A controlled heat stimulus is applied to the feet of mice on a ⅛-inch thick aluminum plate. A 250 watt reflector infrared heat lamp is placed under the bottom of the aluminum plate. A thermal regulator, connected to thermistors on the plate surface, programs the heat lamp to maintain a constant temperature of 57° C. Each mouse is dropped into a glass cylinder (6½-inch diameter) resting on the hot plate, and timing is begun when the animal's feet touch the plate. The mouse is observed at 0.5 and 2 hours after treatment with the test compound for the first "flicking" movements of one or both hind feet, or until 10 seconds elapse without such movements. Morphine has an MPE$_{50}$=4–5.6 mg./kg. (s.c.).

(b) Mouse Tail Flick Analgesic Testing

Tail flick testing in mice is modified after D'Amour and Smith, *J. Pharmacol. Exp. Ther.*, 72, 74–79 (1941) using controlled high intensity heat applied to the tail. Each mouse is placed in a snug-fitting metal cylinder, with the tail protruding through one end. This cylinder is arranged so that the tail lies flat over a concealed heat lamp. At the onset of testing an aluminum flag over the lamp is drawn back, allowing the light beam to pass through the slit and focus onto the end of the tail. A timer is simultaneously activated. The latency of a sudden flick of the tail is ascertained. Untreated mice usually react within 3–4 seconds after exposure to the lamp. The end point for protection is 10 seconds. Each mouse is tested at 0.5 and 2 hours after treatment with morphine and the test compound. Morphine has an $MPE_{50}$ of 3.2–5.6 mg./kg. (s.c.).

(c) Tail Immersion Procedure

The method is a modification of the receptable procedure developed by Benbasset, et al., *Arch. int. Pharmacodyn.*, 122, 434 (1959). Male albino mice (19–21 g.) of the Charles River CD-1 strain are weighed and marked for identification. Five animals are normally used in each drug treatment group with each animal serving as its own control. For general screening purposes, new test agents are first administered at a dose of 56 mg./kg. intraperitoneally or subcutaneously, delivered in a volume of 10 ml./kg. Preceding drug treatment and at 0.5 and 2 hours post drug, each animal is placed in the cylinder. Each cylinder is provided with holes to allow for adequate ventilation and is closed by a round nylon plug through which the animal's tail protrudes. The cylinder is held in an upright position and the tail is completely immersed in the constant temperature waterbath (56° C.). The endpoint for each trial is an energetic jerk or twitch of the tail coupled with a motor response. In some cases, the endpoint may be less vigorous post drug. To prevent undue tissue damage, the trial is terminated and the tail removed from the waterbath within 10 seconds. The response latency is recorded in seconds to the nearest 0.5 second. A vehicle control and a standard of known potency are tested concurrently with screening candidates. If the activity of a test agent has not returned to baseline values at the 2-hour testing point, response latencies are determined at 4 and 6 hours. A final measurement is made at 24 hours if activity is still observed at the end of the test day.

TEST USING CHEMICAL NOCICEPTIVE STIMULI

Suppression of Phenylbenzoquinone Irritant-Induced Writhing

Groups of 5 Carworth Farms CF-1 mice are pretreated subcutaneously or orally with saline, morphine, codeine or the test compound. Twenty minutes (if treated subcutaneously) of fifty minutes (if treated orally) later, each group is treated with intraperitoneal injection of phenylbenzoquinone, an irritant known to produce abdominal contractions. The mice are observed for 5 minutes for the presence or absence of writhing starting 5 minutes after the injection of the irritant. $MPE_{50}$'s of the drum pretreatments in blocking writhing are ascertained.

TESTS USING PRESSURE NOCICEPTIVE STIMULI

Effect on the Haffner Tail Pinch Procedure

A modification of the procedure of Haffner, *Experimentelle Prufung Schmerzstillender. Mittel Deutch Med. Wschr.*, 55, 731–732 (1929) is used to ascertain the effects of the test compound on aggressive attacking responses elicited by a stimulus pinching the tail. Male albino rats (50–60 g.) of the Charles River (Sprague-Dawley) CD strain are used. Prior to drug treatment, and again at 0.5, 1, 2 and 3 hours after treatment, a Johns Hopkins 2.5-inch "bulldog" clamp is clamped onto the root of the rat's tail. The endpoint at each trail is clear attacking and biting behavior directed toward the offending stimulus, with the latency for attack recorded in seconds. The clamp is removed in 30 seconds if attacking has not yet occurred, and the latency of response is recorded as 30 seconds. Morphine is active at 17.8 mg./kg. (i.p.).

TESTS USING ELECTRICAL NOCICEPTIVE STIMULI

The "Flinch-Jump" Test

A modification of the flinch-jump procedure of Tenen, *Psychopharmacologia*, 12, 278–285 (1968) is used for determining pain thresholds. Male albino rats (175–200 g.) of the Charles River (Sprague-Dawley) CD strain are used. Prior to receiving the drug, the feet of each rat are dipped into a 20% glycerol/saline solution. The animals are then placed in a chamber and presented with a series of 1-second shocks to the feet which are delivered in increasing intensity at 30-second intervals. These intensities are 0.26, 0.39, 0.52, 0.78, 1.05, 1.31, 1.58, 1.86, 2.13, 2.42, 2.72 and 3.04 mA. Each animal's behavior is rated for the presence of (a) flinch, (b) squeak and (c) jump or rapid forward movement at shock onset. Single upward series of shock intensities are presented to each rat just prior to, and at 0.5, 2, 4 and 24 hours subsequent to drug treatment.

Results of the above tests are recorded as percent maximum possible effect (%MPE). The %MPE of each group is statistically compared to the %MPE of the standard and the predrug control values. The %MPE is calculated as follows:

$$\% MPE = \frac{\text{test time} - \text{control time}}{\text{cutoff time} - \text{control time}} \times 100$$

The analgesic activity of certain compounds of this invention as determined by the phenylbenzoquinone irritant-induced writhing (PBQ) test described above is presented below. Table I presents data for compounds having the formula

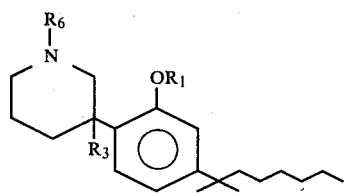

and Table II, for compounds having the formula

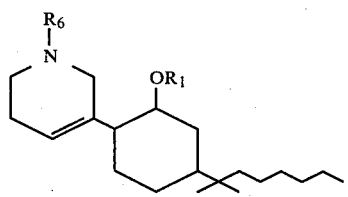

Analgesic Activity $ED_{50}$ (mg./kg.) or % Protection (mg./kg.) Subcutaneously

TABLE I

| $R_6$ | $R_1$ | $R_3$ | PBQ |
|---|---|---|---|
| benzyl | benzyl | OH | 59(56) |

TABLE I-continued

| $R_6$ | $R_1$ | $R_3$ | PBQ |
|---|---|---|---|
| H | H | H | 49(56)* |
| H | H | H | ≧56 |
| $CH_2C\equiv CH$ | H | H | 53(10) |
| $CH_2C\equiv CH$ | H | H | 3.78 |

TABLE II

| $R_6$ | $R_1$ | PBQ |
|---|---|---|
| benzyl | benzyl | >56 |
| benzyl | H | 34.9(56) |
| H | H | 32(56)* |
| $CH_3$ | H | 23(56) |
| $CH_3$ | H | 53(56)* |
| $CH_2C\equiv CH$ | H | 1.65 |
| $CH_2C\equiv CH$ | H | 0.75* |

*HCl salt

The compounds of the present invention are active analgesics via oral and parenteral administration and are conveniently administered in composition form. Such compositions include a pharmaceutical carrier selected on the basis of the chosen route of administration and standard pharmaceutical practice. For example, they can be administered in the form of tablets, pills, powders or granules containing such excipients as starch, milk sugar, certain types of clay, etc. They can be administered in capsules, in admixtures with the same or equivalent excipients. They can also be administered in the form of oral suspensions, solutions, emulsions, syrups and elixirs which may contain flavoring and coloring agents. For oral administration of the therapeutic agents of this invention, tablets or capsules containing from about 0.20 to about 100 mg. are suitable for most applications.

The physician will determine the dosage which will be most suitable for an individual patient and it will vary with the age, weight and response of the particular patient and the route of administration. Generally, however, the initial analgesic dosage in adults may range from about 1.0 to about 750 mg. per day in single or divided doses. In many instances, it is not necessary to exceed 100 mg. daily. The favored oral dosage range is from about 1.0 to about 300 mg./day; the preferred range is from about 1.0 to about 50 mg./day. The favored parenteral dose is from about 0.1 to about 100 mg./day; the preferred range from about 0.1 to about 20 mg./day.

This invention also provides pharmaceutical compositions, including unit dosage forms, valuable for the use of the herein described compounds as analgesics and other utilities disclosed herein. The dosage form can be given in single or multiple doses, as previously noted, to achieve the daily dosage effective for a particular utility.

The compounds (drugs) described herein can be formulated for administration in solid or liquid form for oral or parenteral administration. Capsules containing drugs of this invention are prepared by mixing one part by weight of drug with nine parts of excipient such as starch or milk sugar and then loading the mixture into telescoping gelatin capsules such that each capsule contains 100 parts of the mixture. Tablets containing said compounds are prepared by compounding suitable mixtures of drug and standard ingredients used in preparing tablets, such as starch, binders and lubricants, such that each tablet contains from 0.10 to 100 mg. of drug per tablet.

Suspensions and solutions of these drugs are frequently prepared just prior to use in order to avoid problems of stability of the drug (e.g. oxidation) or of suspensions or solution (e.g. precipitation) of the drug upon storage. Compositions suitable for such are generally dry solid compositions which are reconstituted for injectable administration.

Their activity as diuretic agents is determined by the procedure of Lipschitz et al., *J. Pharmacol.*, 197, 97 (1943) which utilizes rats as the test animals. The dosage range for this use is the same as that noted above with respect to the use of the herein described compounds as analgesic agents.

Antidiarrheal utility is determined by a modification of the procedure of Neimegeers et al., *Modern Pharmacology-Toxicology*, Willem van Bever and Harbans Lal, Eds., 7, 68–73 (1976). Charles River CD-1 rats (170–200 gms) are housed in group cages 18 hours before testing. The animals are fasted overnight with water available ad libitum prior to administration of castor oil. The test drug is administered subcutaneously or orally at a constant volume of 5 ml./kg. of body weight in a 5% Emulphor EL-620 (a polyoxyethylated vegetable oil emulsifying agent available from Antara Chemicals, New York, N.Y.), and 90% saline vehicle followed one hour later with a challenge of castor oil (one ml., orally). The animals are placed in small individual cages (20.5×16×21 cm.) having suspended wire floors. A disposable cardboard sheet is placed beneath the wire floors and examined one hour after castor oil challenge for the presence or absence of diarrhea. A vehicle/castor oil treatment group serves as control for each day's testing. Results are recorded as the number of animals protected at one hour post challenge. In general, the dosage levels for use of these compounds as antidiarrheal agents parallels those with respect to their use as analgesic agents.

The tranquilizer activity of the compounds of this invention is determined by orally administering them to rats at doses of from about 0.01 to about 50 mg./kg. of body weight and observing the subsequent decreases in spontaneous motor activity. The daily dosage range in mammals is from about 0.01 to about 100 mg.

Anticonvulsant activity is determined by subcutaneously administering the test compound to male Swiss mice (Charles River) weighing 14–23 g. in a vehicle of the type used for antidiarrheal activity. The mice are used in groups of five. The day before use, the mice are fasted overnight but watered ad lib. Treatments are given at volumes of 10 ml. per kg. via a 25 gauge hypodermic needle. Subjects are treated with the test compound and, one hour after challenge, electroconvulsive shock, 50 mA. at 60 Hz. administered transcorneally. Controls are simultaneously run in which the mice are given only the vehicle as control treatment. The electroconvulsive shock treatment produces tonic extensor convulsions in all control mice with a latency of 1.5–3 seconds. Protection is recorded when a mouse exhibits no tonic extensor convulsions for 10 seconds after administration of electroconvulsive shock.

Antianxiety activity is determined in a manner similar to that for evaluating anticonvulsant activity except that the challenge convulsant is pentylenetetrazole, 120 mg./kg. administered intraperitoneally. This treatment produces clonic convulsions in less than one minute in over 95% of control mice treated. Protection is recorded when the latency to convulse is delayed at least 2-fold by a drug pretreatment.

Sedative/depressant activity is determined by treating groups of six mice subcutaneously with various doses of test agents. At 30 and 60 minutes post treatment, the mice are placed on a rotorod for one minute and evaluated for their performance on the rotorod. Inability of the mice to ride the rotorod is taken as evidence of sedative/depressant activity.

EXAMPLE 1

1-Benzyl-3-[2-benzyloxy-4-(1,1-dimethylheptyl)-phenyl]-3-hydroxypiperidine

A solution of 20.0 g. (51.4 mmols) of 1-bromo-2-benzyloxy-4-(1,1-dimethylheptyl)benzene in 75 ml. of tetrahydrofuran is slowly added to 2.5 g. (103 mmols) of 70–80 mesh magnesium metal. The resulting mixture is refluxed for 20 minutes and is then cooled to −10° C. A solution of 9.71 g. (51.4 mmols) of N-benzyl-3-piperidone in 25 ml. of tetrahydrofuran is then added at such a rate that the reaction temperature is maintained below 0° C. The reaction mixture is stirred for 30 minutes following completion of addition and is then added to 500 ml. of saturated ammonium chloride and 500 ml. of ether. The ether extract is washed with two 250 ml. portions of sodium chloride, dried over magnesium sulfate and evaporated to an oil. The oil is purified via column chromatography on 700 g. of silica gel eluted with 50% ether-cyclohexane to yield 17.1 g. (67%) of the title compound as an oil:

PMR: $\delta_{CDCl_3}^{TMS}$ 0.85 (m, terminal sidechain methyl), 1.25 (s, gem dimethyl), 3.05 (m, C-2 piperidine methylene), 3.10 (s, OH), 3.63 (bs, N-benzyl methylene), 5.02 (s, benzyl ether methylene), 6.81 (bs, overlaps $\delta$6.85, ArH), 6.85 (dd, J=8 and 2 Hz, ArH), 7.60 (d, J=8 Hz, ArH), 7.25 (s, PhH) and 7.32 (s, PhH).

IR: (CHCl₃) 3448, 1618 and 1572 cm⁻¹.

MS: m/e 499 (M+), 481, 408 and 390.

In like manner, the following compounds are prepared from appropriate 1-bromo-2-benzyloxy-4-(Z-W)benzenes and azacycloalkan-3-ones:

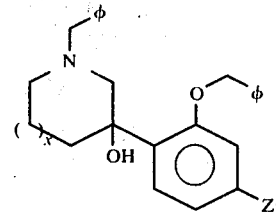

| x | Z | W |
|---|---|---|
| 0, 1, 2 | CH(CH₃)CH(CH₃)(CH₂)₅ | H |
| 0, 1 | (CH₂)₅ | H |
| 0, 1 | CH(CH₃)(CH₂)₂ | C₆H₅ |
| 0, 1, 2, 3 | CH(CH₃)(CH₂)₃ | C₆H₅ |
| 1, 2 | CH(CH₃)(CH₂)₄ | 4-FC₆H₄ |
| 0, 1, 3 | O(CH₂)₄ | C₆H₅ |
| 1, 2 | OCH(CH₃)(CH₂)₃ | C₆H₅ |
| 1, 2 | OCH(CH₃)(CH₂)₃ | 4-ClC₆H₄ |
| 0, 1 | (CH₂)₁₀ | C₆H₅ |
| 0, 1, 3 | (CH₂)₁₃ | H |
| 1, 3 | O(CH₂)₆ | H |
| 1 | O(CH₂)₁₀ | 3-pyridyl |
| 0, 1, 2 | CH(CH₃)(CH₂)₃ | 4-pyridyl |
| 1 | (CH₂)₅O(CH₂)₈ | H |
| 1, 3 | CH(CH₃)(CH₂)₂O | C₆H₅ |
| 0, 2, 3 | C(CH₃)₂(CH₂)₆ | H |
| 0, 1 | O(CH₂)₄ | C₆H₅ |
| 0, 3 | CH(C₂H₅)(CH₂)₄ | 4-FC₆H₄ |
| 0, 2 | OC(CH₃)₂(CH₂)₁₀ | 4-FC₆H₄ |

-continued

| x | Z | W |
|---|---|---|
| 0, 1 | O(CH₂)₅ | 3-pyridyl |
| 1, 2 | O(CH₂)₁₀ | 4-ClC₆H₄ |
| 0, 1, 2 | CH(CH₃)CH₂—O—CH₂ | H |
| 1 | CH(CH₃)CH₂OCH₂ | C₆H₅ |
| 0, 2 | CH₂CH(CH₃)O(CH₂)₂ | 4-FC₆H₄ |

For convenience, various values of x for given values of Z and W are collectively tabulated.

EXAMPLE 2

3-[4-(1,1-Dimethylheptyl)-2-hydroxyphenyl]-3-piperidinol

A mixture of 8.5 g. (17.03 mmols) of 1-benzyl-3-[2-benzyloxy-4-(1,1-dimethylheptyl)phenyl]-3-hydroxypiperidine, 2.0 g. of 10% palladium-on-carbon and 60 ml. of ethanol is stirred under one atmosphere of hydrogen for 2 hours. The reaction mixture is filtered through diatomaceous earth with ethyl acetate and evaporated. The residue is recrystallized from ethyl acetate to yield 3.8 g. (70%) of the title compound. A second crop of the title compound 0.396 g. (7%) is obtained from the mother liquor.

M.P.: 147° C.

PMR: $\delta_{CDCl_3}^{TMS}$ 0.85 (m, terminal sidechain methyl), 1.24 (s, gem dimethyl), 3.08 (bs, C-2 piperidine methylene), 6.3 (bs, exchangeable H), 6.8 (m, ArH) and 7.20 (d, J=8 Hz, ArH).

IR: (KBr) 3413, 3236 and 1613 cm⁻¹.

MS: m/e 319 (M+), 301, 286, 234 and 216.

Analysis: Calc'd for C₂₀H₃₃NO₂: C, 75.19; H, 10.41; N, 4.38%. Found C, 75.35; H, 10.13; N, 4.39%.

In like manner, the compounds listed in Example 1 are debenzylated to give compounds having the formula below wherein x and Z-W are as defined in Example 1.

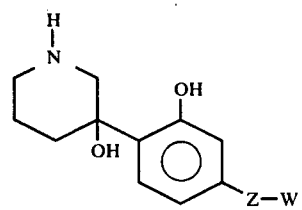

EXAMPLE 3

3-[4-(1,1-Dimethylheptyl)-2-hydroxyphenyl]-1,2,5,6-tetrahydropyridine

A mixture of 23.6 g. (74.2 mmoles) of 3-[4-(1,1-dimethylheptyl)-2-hydroxyphenyl]-3-piperidinol and 400 ml. of 2 N hydrochloric acid is heated at reflux for 2 hours. The reaction is cooled, evaporated and dissolved in excess saturated sodium bicarbonate and 400 ml. of dichloromethane. The dichloromethane extract is combined with a second 400 ml. dichloromethane extract of the aqueous phase, dried over magnesium sulfate and evaporated to an oil. Crystallization from ether-pentane gave 13.0 g. (58%) of the title compound.
M.P.: 122°-123° C.
PMR: $\delta_{CDCl_3}^{TMS}$ 0.84 (m, terminal methyl), 1.10 (s, gem dimethyl), 2.50 (m, C-5 methylene), 3.32 (bt, J=6 Hz, C-6 methylene), 4.00 (bs, C-2 methylene), 5.90 (m, vinyl proton), 6.9 (m, ArH) and 8.42 (bs, OH, NH).
IR: (KBr) 3448, 3289, 1613 and 1575 cm$^{-1}$.
MS: m/e 301 (M+), 286, 272, 258 and 216.

Neutralization of this compound in ether with ethanolic hydrogen chloride gives the HCl salt, M.P. 156° C. (from ether-ethanol).

Similarly, the compounds of Example 2 are dehydrated to corresponding compounds having the formula:

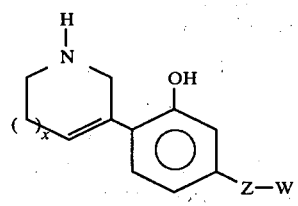

EXAMPLE 4

1-Benzyl-3-[2-benzyloxy-4-(1,1-dimethylheptyl)-phenyl]-1,2,5,6-Tetrahydropyridine and the Free Phenol A mixture of 7.0 g. (14.0 mmols) of 1-benzyl-3-[2-benzyloxy-4-(1,1-dimethylheptyl)phenyl]-3-hydroxypiperidine and 200 ml. of 2 N hydrochloric acid is heated at reflux for 6 hours. The reaction mixture is evaporated under reduced pressure to a thick residue which is dissolved in 500 ml. of saturated sodium bicarbonate-300 ml. of ether-100 ml. of dichloromethane. The organic phase is separated, dried over magnesium sulfate and evaporated to an oil. The oil is purified via column chromatography on 400 g. of silica gel eluted with 50% ether-cyclohexane to yield, in order of elution, 5.1 g. (76%) of the title compound as an oil and 1.32 g. (24%) of 1-benzyl-3-[4-(1,1-dimethylheptyl)-2-hydroxyphenyl]-1,2,5,6-tetrahydropyridine as an oil.

Title Compound

PMR: $\delta_{CDCl_3}^{TMS}$ 0.87 (m, terminal sidechain methyl), 1.28 (s, gem dimethyl), 2.48 (m, C-5 methylene of pyridine), 2.88 (m, C-6 methylene of pyridine), 3.61 (bs, N-benzyl methylene), 3.82 (bs, C-2 methylene of pyridine), 5.10 (s, benzyl ether methylene), 5.93 (m, vinyl H), 6.8-7.3 (m, ArH) and 7.3-7.6 (m, PhH).
IR: (CHCl$_3$) 1653, 1610 and 1565 cm$^{-1}$.
MS: m/e 481 (M+), 396, 390 and 91.

Phenolic Compound

PMR: $\delta_{CDCl_3}^{TMS}$ 0.82 (m, terminal sidechain methyl), 1.22 (s, gem dimethyl), 2.40 (m, C-5 methylene of pyridine), 2.88 (t, J=6 Hz, C-6 methylene of pyridine), 3.42 (bs, N-benzyl methylene), 3.82 (s, C-2 methylene of pyridine), 5.87 (m, vinyl H), 6.6-7.1 (m, ArH) and 7.1-7.4 (m, PhH).
IR: (CHCl$_3$) 3509, 3175, 1667, 1623 and 1608 cm$^{-1}$.
MS: m/e 391 (M+), 376, 306, 300, 272, 187, 120 and 91.

Similarly, the following compounds are prepared from appropriate 1-bromo-2-benzyloxy-4-(Z-W)benzenes and the appropriate azacycloalkan-3-one according to the procedure of Example 1 and the above procedure. The free phenol is also produced. ($\phi$=phenyl)

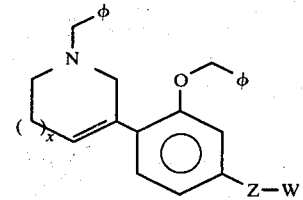

| x* | Z | W |
|---|---|---|
| 0, 1, 3 | C(CH$_3$)$_2$(CH$_2$)$_2$ | H |
| 1, 2 | C(CH$_3$)$_2$(CH$_2$)$_{10}$ | H |
| 1, 2 | C(CH$_3$)$_2$(CH$_2$)$_4$ | C$_6$H$_5$ |
| 1 | C(CH$_3$)$_2$(CH$_2$)$_{10}$ | C$_6$H$_5$ |
| 0, 1, 2 | C(CH$_3$)$_2$(CH$_2$)$_4$ | 4-pyridyl |
| 0, 1 | C(CH$_3$)$_2$(CH$_3$)$_3$ | 2-pyridyl |
| 1, 3 | CH(CH$_3$)(CH$_2$)$_2$ | C$_6$H$_5$ |
| 1, 3 | CH(C$_2$H$_5$)(CH$_2$)$_2$ | 4-ClC$_6$H$_4$ |
| 0, 1 | CH(C$_2$H$_5$)(CH$_2$)$_4$ | 4-FC$_6$H$_4$ |
| 2 | (CH$_2$)$_5$ | H |
| 1, 2 | OCH(CH$_3$)(CH$_2$)$_3$ | 4-ClC$_6$H$_4$ |
| 1 | (CH$_2$)$_{13}$ | H |
| 1 | (CH$_2$)$_4$ | C$_6$H$_5$ |
| 0, 1 | (CH$_2$)$_8$ | H |
| 2 | (CH$_2$)$_3$ | 2-pyridyl |
| 1, 3 | (CH$_2$)$_4$ | 4-pyridyl |
| 2 | CH(CH$_3$)CH(CH$_3$)CH$_2$ | 3-pyridyl |
| 2 | CH(CH$_3$)CH(CH$_3$)CH$_2$ | 4-pyridyl |
| 0, 1 | CH(C$_2$H$_5$)(CH$_2$)$_2$ | 4-pyridyl |
| 0, 2 | (CH$_2$)$_{10}$ | 4-pyridyl |
| 0, 1, 2, 3 | OCH(CH$_3$)(CH$_2$)$_3$ | C$_6$H$_5$ |
| 1, 3 | O | C$_6$H$_5$ |
| 0, 1 | O | 4-FC$_6$H$_4$ |
| 1, 2 | O | 4-ClC$_6$H$_4$ |
| 1 | O(CH$_2$)$_4$ | 4-FC$_6$H$_4$ |
| 2 | O(CH$_2$)$_8$ | C$_6$H$_5$ |
| 2 | O(CH$_2$)$_{10}$ | 4-ClC$_6$H$_4$ |
| 0, 2 | OCH(CH$_3$)(CH$_2$)$_8$ | C$_6$H$_5$ |
| 1 | OCH(CH$_3$)CH$_2$ | 4-FC$_6$H$_4$ |
| 1 | OC(CH$_3$)$_2$(CH$_2$)$_3$ | C$_6$H$_5$ |
| 2 | OCH$_2$CH(CH$_3$)CH$_2$ | C$_6$H$_5$ |
| 0, 3 | OCH(CH$_3$)(CH$_2$)$_{10}$ | H |
| 2 | (CH$_2$)$_3$O | 3-pyridyl |
| 1 | OC(CH$_3$)$_2$(CH$_2$)$_7$ | H |
| 1 | O(CH$_2$)$_{13}$ | H |
| 1, 2 | O(CH$_2$)$_{13}$ | C$_6$H$_5$ |
| 3 | OCH(CH$_3$)(CH$_2$)$_6$ | 4-FC$_6$H$_4$ |
| 3 | OC(CH$_3$)$_2$(CH$_2$)$_{10}$ | 4-FC$_6$H$_4$ |
| 2 | (CH$_2$)$_3$OCH(CH$_3$) | 2-pyridyl |
| 1 | OCH(C$_2$H$_5$)(CH$_2$)$_3$ | 4-ClC$_6$H$_4$ |
| 0 | OC(CH$_3$)$_2$(CH$_2$)$_6$ | H |
| 2 | O(CH$_2$)$_2$C(CH$_3$)$_2$(CH$_2$)$_2$ | H |
| 0 | O(CH$_2$)$_6$ | C$_6$H$_5$ |
| 3 | O(CH$_2$)$_{12}$ | H |
| 0, 1, 3 | OCH(CH$_3$)(CH$_2$)$_3$ | 4-pyridyl |
| 1 | O(CH$_2$)$_2$ | 4-pyridyl |
| 1, 2 | OCH(CH$_3$)(CH$_2$)$_3$ | 2-pyridyl |
| 0 | O(CH$_2$)$_5$ | 3-pyridyl |
| 1, 2 | O | 4-pyridyl |
| 0 | OCH(C$_2$H$_5$)(CH$_2$)$_2$ | 4-pyridyl |
| 0, 1 | O(CH$_2$)$_{10}$ | 2-pyridyl |
| 1 | (CH$_2$)$_3$O(CH$_2$)$_3$ | H |
| 1 | CH(CH$_3$)(CH$_2$)$_2$O(CH$_2$)$_4$ | 4-pyridyl |
| 1, 2 | (CH$_2$)$_2$O(CH$_2$)$_8$ | H |
| 0, 1 | (CH$_2$)$_6$OCH(CH$_3$) | H |
| 0 | CH(C$_2$H$_5$)(CH$_2$)$_2$OCH(CH$_3$) | 2-pyridyl |
| 0, 3 | (CH$_2$)$_2$O(CH$_2$)$_{10}$ | H |
| 0, 3 | (CH$_2$)$_{10}$O(CH$_2$)$_2$ | H |
| 1, 3 | C(CH$_3$)$_2$(CH$_2$)$_2$O(CH$_2$)$_4$ | H |
| 0 | (CH$_2$)$_4$OCH$_2$ | C$_6$H$_5$ |
| 1 | CH(CH$_3$)(CH$_2$)$_2$O | C$_6$H$_5$ |
| 1, 2 | (CH$_2$)$_{13}$O | H |
| 1 | (CH$_2$)$_6$O | H |
| 0 | (CH$_2$)$_6$OCH$_2$ | 4-ClC$_6$H$_4$ |

-continued

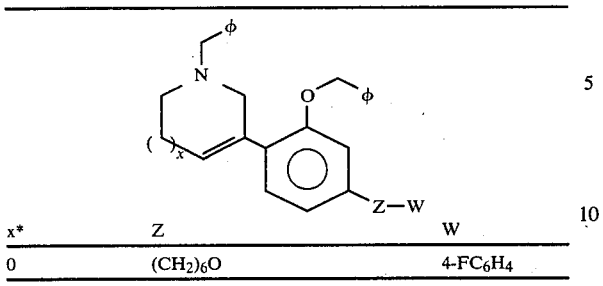

| x* | Z | W |
|---|---|---|
| 0 | (CH₂)₆O | 4-FC₆H₄ |

*Multiple values listed under column "x" indicate preparation of compounds having the given values of Z and W.

EXAMPLE 5

3-[4-(1,1-Dimethylheptyl)-2-hydroxyphenyl]piperidine

A mixture of 7.4 g. (24.5 mmoles) of 3-[4-(1,1-dimethylheptyl)-2-hydroxyphenyl]-1,2,5,6-tetrahydropyridine and 2.0 g. of 10% palladium-on-carbon in 150 ml. of ethanol and 75 ml. of ethyl acetate is stirred under one atmosphere of hydrogen for 2.5 hours. The reaction is filtered through diatomaceous earth and evaporated. Crystallization of the residue from ether-pentane gave 4.6 g. (62%) of the title compound.

M.P.: 138°–140° C.

PMR: $\delta_{CDCl_3}$ $^{TMS}$ 0.80 (m, terminal methyl), 1.21 (s, gem dimethyl), 6.85 (m, ArH) and 8.7 (bs, NH, OH).

MS: m/e 303 (M+), 288, 260, 218 and 175.

IR: (KBr) 3333 (broad), 1623 and 1592 cm⁻¹.

Neutralization of the compound in ether with ethanolic-hydrogen chloride gives the HCl salt as a hygroscopic glass after vacuum drying.

The remaining 1,2,5,6-tetrahydropyridines of Example 3 are similarly reduced to the corresponding compounds having the formula:

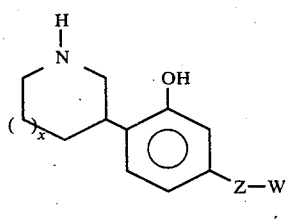

EXAMPLE 6

3-[4-(1,1-Dimethylheptyl)-2-hydroxyphenyl]piperidine

A mixture of 4.2 g. (8.73 mmols) of 1-benzyl-3-[2-benzyloxy-4-(1,1-dimethoxyheptyl)phenyl]-1,2,5,6-tetrahydropyridine, 4.0 g. of 10% palladium-on-carbon and 50 ml. of ethanol is stirred under one atmosphere of hydrogen for 2 hours. The reaction mixture is filtered through diatomaceous earth with ethyl acetate, evaporated and the residue again dissolved in ethyl acetate and filtered. The filtrate is evaporated and the residue crystallized in ether to yield 1.1 g. (42%) of the title compound.

The product is identical to that of Example 5.

In like manner, hydrogenation of the compounds listed in Example 3 affords the corresponding compounds having the formula below wherein -Z-W and x are as defined in Example 4.

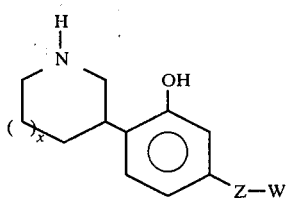

EXAMPLE 7

1-Benzyl-3-[2-benzyloxy-4-(1,1-dimethylheptyl)phenyl-4-piperidinol

To a mixture of 39.9 g. (80 mmols.) of 1-benzyl-3-[2-benzyloxy-4-(1,1-tetrahydropyridine and 4.8 g. (115 mmols.) of sodium borohydride in 50 ml. of tetrahydrofuran is added 21.6 ml. (180 mmols.) of borontrifluoride etherate complex in 40 ml. of tetrahydrofuran during a 2 hour period at 0°–5° C. Stirring is continued 2 hours longer at 25° C. The reaction mixture is cooled in ice and quenched with 6.5 ml. of water and then 20 ml. of 2 N sodium hydroxide and 20 ml. of 30% hydrogen peroxide are added dropwise. After several minutes stirring the reaction is cooled and 20 ml. of concentrated hydrochloric acid is added dropwise. The reaction mixture is partially evaporated and then made basic with 6 N sodium hydroxide. The concentrated mixture is extracted with 250 ml. of ether, the ether extract washed with 100 ml. of saturated sodium chloride, dried over magnesium sulfate and evaporated. The residue is purified via column chromatography on 400 g. of silica gel eluted with 50% ether-cyclohexane to yield the title compound.

Repetition of the above procedure but using the appropriate 1,2,5,6-tetrahydropyridine reactants (Example 4) affords 4-piperidinols having the formula below wherein -Z-W and x are as defined in Example 4:

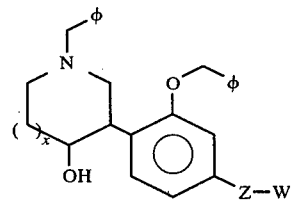

EXAMPLE 8

1-Benzyl-3-[2-benzyloxy-4-(1,1-dimethylheptyl)-phenyl]-4-piperidone

To a cooled solution of 24.8 g. (50 mmols.) of 1-benzyl-3-[2-benzyloxy-4-(1,1-dimethylheptyl)phenyl]-4-piperidinol, 100 ml. of acetone, 6.0 g. (60 mmols.) of chromium trioxide, 15 ml. of water and 20 ml. of acetic acid is added dropwise 20 ml. of concentrated sulfuric acid at such a rate as to maintain the temperature at 5° C. The reaction mixture is stirred 5 hours longer (t < 18° C.) and then neutralized with concentrated ammonium hydroxide. The reaction mixture is extracted with 500 ml. of ether, the ether extract washed once with saturated sodium chloride, dried over magnesium sulfate and evaporated. Purification is accomplished via rapid column chromatography on 100 g. of silica gel eluted with ether to yield the title compound.

Oxidation of the 4-piperidinol compounds of Example 7 by means of the above procedure provides corresponding 4-piperidones having the formula below wherein -Z-W and x are as defined in Example 7:

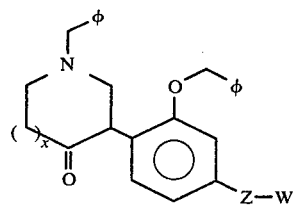

EXAMPLE 9

1-($R_6'$-substituted)-3-[2-benzyloxy-4-(Z-W)phenyl]-$\Delta^3$-azacycloalkenes

The compounds tabulated below are prepared from appropriate 1-$R_6'$-azacycloalkan-3-ones of Preparation Y and appropriate 1-bromo-2-benzyloxy-4-(Z-W)benzenes according to the procedure of Example 4:

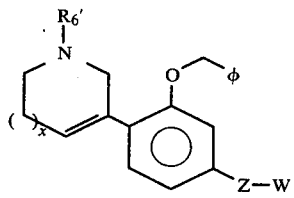

$R_6'$ and x are as defined in Preparation Y and Z and W have the following values:

| Z | W |
|---|---|
| C(CH$_3$)$_2$(CH$_2$)$_6$ | H |
| CH(CH$_3$)CH(CH$_3$)(CH$_2$)$_5$ | H |
| (CH$_2$)$_5$ | H |
| (CH$_2$)$_{13}$ | H |
| CH(CH$_3$)(CH$_2$)$_3$ | C$_6$H$_5$ |
| CH(CH$_3$)(CH$_2$)$_3$ | 4-FC$_6$H$_4$ |
| CH(CH$_3$)(CH$_2$)$_2$ | C$_6$H$_5$ |
| CH(CH$_3$)(CH$_2$)$_2$ | 4-ClC$_6$H$_4$ |
| CH(CH$_3$)(CH$_2$)$_4$ | 4-ClC$_6$H$_4$ |
| CH(CH$_3$)(CH$_2$)$_3$ | 4-pyridyl |
| CH(CH$_3$)(CH$_2$)$_2$ | 2-pyridyl |
| OCH(CH$_3$)(CH$_2$)$_3$ | C$_6$H$_5$ |
| OCH(CH$_3$)(CH$_2$)$_2$ | 4-FC$_6$H$_4$ |
| OCH(CH$_3$)(CH$_2$)$_3$ | 4-pyridyl |
| O(CH$_2$)$_4$ | C$_6$H$_5$ |
| O(CH$_2$)$_4$ | 4-pyridyl |
| O(CH$_2$)$_{10}$ | 3-pyridyl |
| O | 4-ClC$_6$H$_4$ |
| O | 4-pyridyl |
| (CH$_2$)$_4$O | H |
| (CH$_2$)$_{13}$O | H |
| (CH$_2$)$_6$O | 4-FC$_6$H$_4$ |
| (CH$_2$)$_5$O(CH$_2$)$_8$ | H |
| (CH$_2$)$_4$OCH$_2$ | C$_6$H$_5$ |
| CH(CH$_3$)(CH$_2$)$_2$O | C$_6$H$_5$ |
| (CH$_2$)$_4$O(CH$_2$)$_5$ | 4-pyridyl |

EXAMPLE 10

1-($R_6'$-Substituted)-3-[2-benzyloxy-4-(Z-W)phenyl]-4-azacycloalkanones

The compounds of Example 7 are subjected to the procedures of Examples 7 and 8 to give the following compounds wherein x, $R_6'$, Z and W are as defined in Example 9.

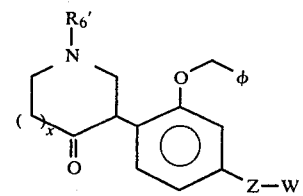

EXAMPLE 11

1-($R_6'$-Substituted)-3-[2-benzyloxy-4-(Z-W)phenyl]-azacyloalkanes

Following the procedure of Example 5, the compounds of Example 7 are converted to compounds having the formula below wherein x, $R_6'$, Z and W are as defined in Example 9.

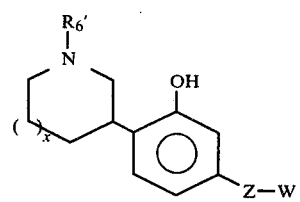

EXAMPLE 12

1-Benzyl-3-[2-benzyloxy-4-(1,1-dimethylheptyl)-phenyl]-4-(3-phenylpropylidene)piperidine To a 15° C. solution of 4.13 g. (12.0 mmols.) of triphenyl 3-phenyl-propylphosphorane in 24 ml. of dimethyl sulfoxide [from 5.10 g. (12.0 mmols.) of triphenyl 3-phenylpropylphosphonium bromide and 12.0 mmols. of dimsyl sodium in 24 ml. of dimethyl sulfoxide] is slowly added 4.97 g. (10.0 mmols.) of 1-benzyl-3-[2-benzyloxy-4-(1,1-dimethylheptyl)phenyl]-4-piperidone in 10 ml. of dimethyl sulfoxide. The reaction mixture is then allowed to warm to 25° C. and is then stirred at 25° C. for 4 hours. It is then added to 500 ml. of ice water-250 ml. ether. The ether extract is washed with two 250 ml. portions of water, dried over magnesium sulfate and evaporated. The residue is purified via column chromatography on 400 g. of silica gel eluted with 50% ether-cyclohexane to yield the title compound.

Repetition of the above procedure but using the appropriate 4-piperidinone compounds of Examples 8 and 10 and the appropriate triphenyl($R_2$)-phosphonium bromide reactant $(C_6H_5)_3P^+R_2'(Br)^-$ affords the following compounds.

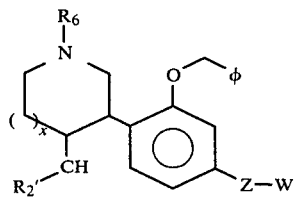

which are hydrogenated according to the procedure of Example 5 to give compounds from Example 8 having formula A and from Example 10, compounds having formula B:

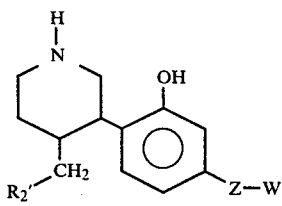

and

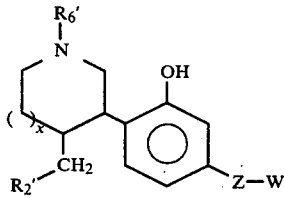

wherein R$_6$ is benzyl or R$_6'$ as defined in Example 10, and x, Z and W are as defined in Examples 8 and 10. R$_2'$ has the values:

| | |
|---|---|
| C$_6$H$_5$ | H |
| CH$_2$C$_6$H$_5$ | CH$_3$ |
| (CH$_2$)$_3$C$_6$H$_5$ | C$_2$H$_5$ |
| n-C$_5$H$_{11}$ | CH$_2$CH(CH$_3$)$_2$ |

The requisite triphenyl(R$_2$)phosphonium bromide reactants are prepared by refluxing an equimolar mixture of triphenylphosphine and R$_2$Br in a suitable solvent, e.g., acetonitrile, for from 1–2 hours. The reaction mixture is cooled and the product recovered by filtration if solid, or by evaporation of solvent if a liquid.

EXAMPLE 13

1-Benzyl-3-[2-benzyloxy-4-(1,1-dimethylheptyl)-phenyl]-4-(3-phenylpropyl)-4-piperidinol To a 0° C. solution of 7.0 mmols. of 3-phenylpropyl-magnesium bromide in 7 ml. of tetrahydrofuran is slowly added a solution of 2.48 g. (5.0 mmols) of 1-benzyl-3-[2-benzyloxy-4-(1,1-dimethylheptyl)phenyl]-4-piperidone in 10 ml. of tetrahydrofuran. The resultant mixture is stirred for one hour and is then added to 250 ml. of saturated ammonium chloride-250 ml. ether. The ether phase is dried over magnesium sulfate and evaporated. The residue is purified via column chromatography on 200 g. of silica gel eluted with 50% ether-cyclohexane to yield the title compound.

The compounds of Examples 8 and 10 are converted to compounds tabulated below by means of the above procedure and the appropriate Grignard reagent wherein x, Z and W are as defined in Examples 8 and 10. R$_6$ is benzyl (Example 8 reactants) and R$_6'$ (Example 10 reactants). R$_2'$ has the values given below.

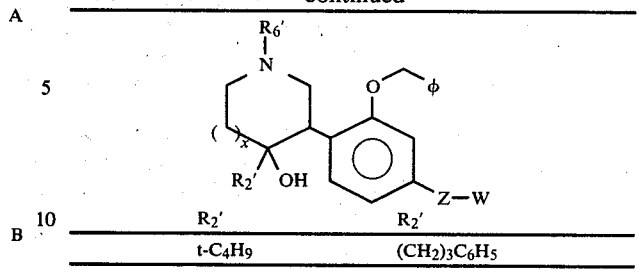

| R$_2'$ | R$_2'$ |
|---|---|
| CH$_3$ | n-C$_6$H$_{13}$ |
| n-C$_3$H$_7$ | C$_6$H$_5$ |
| i-C$_3$H$_7$ | (CH$_2$)C$_6$H$_5$ |
| t-C$_4$H$_9$ | (CH$_2$)$_3$C$_6$H$_5$ |

EXAMPLE 14

1-Benzyl-3-[2-benzyloxy-4-(1,1-dimethylheptyl)-phenyl]-4-(3-phenylpropyl)-1,2,5,6-tetrahydropyridine To a −5° C. solution of 3.0 g. (4.85 mmols.) of 1-benzyl-3-[2-benzyloxy-4-(1,1-dimethylheptyl)phenyl]-4-(3-phenylpropyl)-4-piperidinol in 5 ml. of pyridine is slowly added 2.89 g. (24.3 mmols.) of thionyl chloride. The reaction mixture is then allowed to slowly warm to 25° C. and is stirred 12 hours longers. The reaction mixture is quenched by slow addition to 200 ml. of cold 20% potassium carbonate. The quenched mixture is extracted with 250 ml. of ether, the extract washed once with 200 ml. 20% potassium carbonate, dried over magnesium sulfate and evaporated. THe residue is purified via column chromatography on 300 g. silica gel eluted with 50% ether-cyclohexane to yield the title compound.

In like manner, the compounds of Example 13 are dehydrated to compounds having the formula below wherein R$_6$, R$_2'$ and -Z-W are as defined in Example 13.

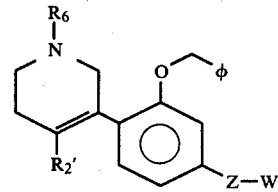

Catalytic hydrogenation of the 1,2,5,6-tetrahydropyridine compounds thus produced over Pd/C affords the corresponding compounds of the formula

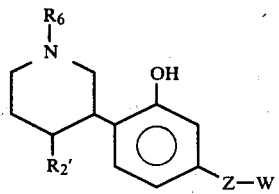

wherein R$_6$ is hydrogen or R$_6'$ as defined in Example 13, other, of course, than benzyl.

EXAMPLE 15

3-[4-(1,1-Dimethylheptyl)-2-hydroxyphenyl]-4-(3-phenylpropyl)-4-piperidinol

A mixture of 6.17 g. (10.0 mmols.) of 1-benzyl-3-[2-benzyloxy-4-(1,1-dimethylheptyl)phenyl]-4-(3-phenylpropyl)-4-piperidinol, 2.0 g. of 10% palladium-on-carbon and 50 ml. of ethanol is stirred under one atmosphere of hydrogen for 2 hours. The reaction mixture is filtered through diatomaceous earth with ethyl acetate and the filtrate evaporated. The residue is purified via crystallization from ether-pentane to yield the title compound.

Similarly, the compounds of Example 13 wherein $R_6$ is benzyl are debenzylated to afford compounds having the following formula wherein $R_2'$, Z, W and x are as defined in Example 13:

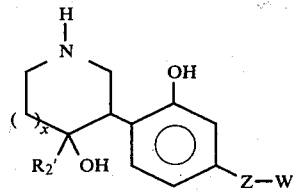

EXAMPLE 16

3-[4-(1,1-Dimethylheptyl)-2-hydroxyphenyl]-4-(3-phenylpropyl)-1,2,5,6-tetrahydropyridine A mixture of 2.0 g. (4.57 mmols.) of 3-[4-(1,1-dimethylheptyl)-2-hydroxyphenyl]-4-(3-phenylpropyl)-4-piperidinol, 0.95 g. (5.0 mmols.) of p-toluenesulfonic acid monohydrate and 100 ml. of toluene is heated under reflux for 2 hours with a Dean Stark trap. The reaction mixture is cooled and added to 100 ml. of 20% potassium carbonate-200 ml. dichloromethane. The dichloromethane extract along with two additional 200 ml. dichloromethane extracts of the basic phase is dried over magnesium sulfate and evaporated. The residue is crystallized from ether-pentane to yield the title compound.

By means of the procedure of Example 15 and the above procedure, Example 13 compounds are converted to the following compounds wherein x, $R_6$, $R_2'$ and -Z-W are as defined in Example 13.

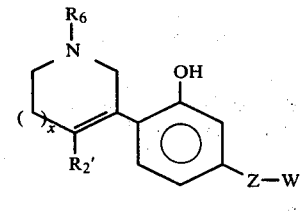

EXAMPLE 17

The following compounds are prepared from the 1-$R_6'$-4-$R_2'$-piperidones of Preparation AA and the appropriate 1-bromo-2-benzyloxy-4-(Z-W)benzene by the procedures of Examples 1, 4 and 5. In the formula below, x, $R_6'$ and $R_2'$ are as defined in Preparation Z, and Z-W is one of the following groups:

—C(CH$_3$)$_2$(CH$_2$)$_5$CH$_3$

—CH(CH$_3$)CH(CH$_3$)(CH$_2$)$_4$CH$_3$

—CH(CH$_3$)(CH$_2$)$_4$C$_6$H$_5$

—OCH(CH$_3$)(CH$_2$)$_3$C$_6$H$_5$

—O(CH$_2$)$_4$C$_6$H$_5$

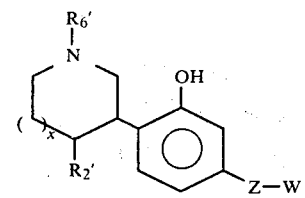

Of course, when $R_6'$ in the 1-$R_6'$-4-$R_2'$-piperidone reactant is benzyl, it is removed in the catalytic hydrogenation step to give $R_6'$=hydrogen.

EXAMPLE 18

3-[4-(1,1-Dimethylheptyl)-2-hydroxyphenyl]-1-N-methyl-1,2,5,6-tetrahydropyridine To a 25° C. solution of 1.0 g. (3.32 mmoles) of 3-[4-(1,1-dimethyl-heptyl)-2-hydroxyphenyl]-1,2,5,6-tetrahydropyridine in 15 ml. of acetonitrile is added 1.32 ml. (17.6 mmoles) of 37% formaldehyde solution. After stirring for one hour the reaction is cooled to 0° C. and 332 mg. (5.3 mmole) of sodium cyanoborohydride added. The reaction mixture is allowed to warm to 25° C. over a one hour period while the pH is maintained at 7 by the addition of acetic acid. The reaction mixture is evaporated, made basic with 2 N potassium hydroxyide and extracted with 200 ml. of dichloromethane. The organic extract is dried over magnesium sulfate and evaporated. The residue is crystallized from ether-pentane to yield 350 mg. of the title compound.

M.P.: 126°–127° C.

PMR: $\delta_{CDCl_3}^{TMS}$ 0.85 (m, terminal methyl), 1.25 (s, gem dimethyl), 2.5 (m, C-5 or C-6 methyl), 2.68 (s, N-CH$_3$), 2.94 (m, C-5 or C-6 methyl), 3.62 (m, C-2 methylene), 5.98 (m, vinyl proton), 6.80 (m, two ArH) and 7.05 (d, J=8 Hz, ArH).

IR: (CHCl$_3$) 3546, 3175, 1689, 1624 and 1565 cm$^{-1}$.

MS: m/e 315 (M+), 300, 272, 257, 230, 187.

The hydrochloride salt, prepared by neutralization of the compound in ether with ethanolic hydrogen chloride, is obtained as a crystalline solid, M.P. 179° C. (from ethanol-ether).

Analysis: Calc'd for C$_{21}$H$_{33}$NO.HCl: C, 71.67; H, 9.73; N, 3.98, Cl, 10.07%. Found: C, 71.54; H, 9.48; N, 3.94; Cl, 10.22%.

By means of this procedure, the following compounds are prepared from appropriate azacycloalkenes of Example 3 and appropriate aldehydes. In the formula below, x, Z and W are as defined in Example 3 and $R_6$ has the values given below.

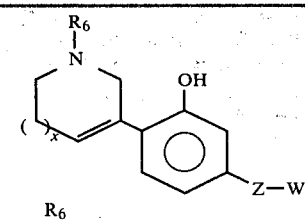

| $R_6$ |
| --- |
| n-C$_3$H$_7$ |
| i-C$_3$H$_7$ |
| n-C$_6$H$_{13}$ |
| (CH$_2$)$_3$C$_6$H$_5$ |
| (CH$_2$)$_4$C$_6$H$_5$ |
| furfuryl |
| 2-thienylmethyl |
| tetrahydrofurfuryl |

| R6 | |
|---|---|
| 2-tetrahydrothienylmethyl | |
| C3H5CH2 | |
| C4H7CH2 | |
| C6H11CH2 | |
| C5H9CH2 | |

| R6 | R6 |
|---|---|
| C2H5 | 2-thienylmethyl |
| i-C4H9 | C3H5CH2 |
| n-C6H13 | C5H9CH2 |
| (CH2)3C6H5 | furfuryl |

Hydrogenation of these compounds according to the procedure of Example 2 but using 5% palladium-on-carbon in place of 10% palladium-on-carbon affords the corresponding saturated compounds.

EXAMPLE 19

3-[4-(1,1-Dimethylheptyl)-2-hydroxyphenyl]-1-N-methylpiperidine

A mixture of 600 mg. (1.98 mmoles) of 3-[4-(1,1-dimethylheptyl)-2-hydroxyphenyl]-piperidine, 0.78 ml. of 37% formaldehyde, 1.98 ml. of 1 N hydrochloric acid and 150 mg. of 5% palladium-on-carbon is hydrogenated under 55 p.s.i. of hydrogen for 1.5 hours. The reaction mixture is filtered through diatomaceous earth and concentrated under reduced pressure. The residue is diluted with 75 ml. of saturated sodium bicarbonate and extracted with two 75 ml. portions of dichloromethane. The combined extract is washed with 75 ml. of saturated sodium chloride, dried over magnesium sulfate and evaporated to yield 567 mg. (90%) of the title compound as an oil.

PMR: $\delta_{CDCl_3}^{TMS}$ 0.80 (m, terminal methyl), 1.25 (s, gem dimethyl), 2.37 (s, N-methyl), 3.05 (m) and 6.75 (m, ArH).

IR: (CHCl3) 3390, 1629 and 1575 cm$^{-1}$.

MS: m/e 317 (M+), 302 and 233.

Neutralization of the compound in ether with ethanolic hydrogen chloride gives the hydrochloride salt, M.P. 198°–199° C. (from ether-ethanol).

Reductive alkylation of compounds of Example 6 according to the above procedure but using the appropriate aldehyde affords the following compounds wherein x, Z and W are as defined in Example 6:

EXAMPLE 20

3-[4-(1,1-Dimethylheptyl)-2-hydroxyphenyl]-1-N-(2-propynyl)piperidine

A mixture of 0.900 g. (2.97 mmoles) of 3-[4-(1,1-dimethylheptyl)-2-hydroxyphenyl]piperidine, 481 mg. (3.49 mmoles) of anhydrous potassium carbonate and 353 mg. (2.97 mmoles) of 1-bromo-2-propyne in 20 ml. of ethanol is heated at reflux for 22 hours. The reaction mixture is then evaporated and dissolved in 100 ml. of saturated sodium bicarbonate and 200 ml. of dichloromethane. The organic extract is washed with two 150 ml. portions of saturated sodium chloride, dried over magnesium sulfate and evaporated. The residue is purified via column chromatography on 100 g. silica gel eluted with 2% methanol-dichloromethane. The product is crystalized from pentane (117 mg., 11.5%).

M.P.: 91°–93° C.

PMR: $\delta_{CDCl_3}^{TMS}$ 0.82 (m, terminal methyl), 1.22 (s, gem dimethyl), 2.41 (t, J=2 Hz, acetylenic methine), 3.57 (d, J=2 Hz, acetylenic methylene) and 6.85 (m, ArH).

IR:(CHCl3) 3356, 1637 and 1582 cm$^{-1}$.

MS: m/e 341 (M+), 326, 257 and 256.

Neutralization of the product in ether with ethanolic hydrogen chloride gives the HCl salt, M.P. 180°–181° C. (from ethanol-ether).

Similarly, the azacycloalkanes of Example 6 are alkylated to give the following compounds wherein x, Z and W are as defined in Example 6 and R6 is:

| R6 | R6 | R6 |
|---|---|---|
| CH2—C≡H | CH(C3H7)C≡CH | (CH2)2—C≡CH |
| (CH2)3—C≡CH | C≡C—(CH2)3CH3 | C≡CH |
| (CH2)2C≡C—CH3 | CH2—C≡C—(CH2)2CH3 | C(CH3)(C2H5)C≡CH |

EXAMPLE 21

3-[4-(1,1-Dimethylheptyl)-2-hydroxyphenyl]-1-N-(2-propynyl)-1,2,5,6-tetrahydropyridine A mixture of 1.0 g. (3.33 mmoles) of 3-[4-(1,1-dimethylheptyl)-2-hydroxyphenyl]-1,2,5,6-tetrahydropyridine, 539 mg. (3.90 mmoles) of anhydrous potassium carbonate and 395 mg. (3.32 mmoles) of 1-bromo-2-propyne in 23 ml. of ethanol is heated at reflux for 20 hours. The reaction mixture is evaporated and dissolved in 100 ml. of saturated sodium bicarbonate and 200 ml. of dichloromethane. The organic extract is washed with two 150 ml. portions of saturated sodium chloride, dried over magnesium sulfate and evaporated. The residue is crystallized from pentane to yield 161 mg. of the title compound.

M.P.: 116°–117° C.

PMR: $\delta_{CDCl_3}{}^{TMS}$ 0.86 (m, terminal methyl), 1.24 (s, gem dimethyl), 2.23 (t, J=2 Hz, acetylenic methine), 2.45 (m, C-5 methylene), 2.78 (t, J=6 Hz, C-6 methylene), 3.33 (m, C-2 methylene), 3.48 (d, J=2 Hz, acetylenic methylene), 5.93 (m, vinyl proton), 6.9 (m, two ArH), and 7.05 (d, J=8 Hz, ArH).

IR: (CHCl$_3$) 3571, 3333, 1637 and 1572 cm$^{-1}$.

MS: m/e 339 (M+), 324, 300, 254 and 187.

Neutralization of the compound in ether with ethanolic hydrogen chloride gives the hydrochloride salt, M.P. 158° C. (from ether-ethanol).

Analysis: Calc'd for $C_{23}H_{33}NO \cdot HCl$: C, 73.48; H, 9.12; N, 3.72%. Found: C, 73.37; H, 8.91; N, 3.73%.

The following compounds are prepared in like manner by the above procedure from appropriate alkynyl bromides and compounds of Example 3:

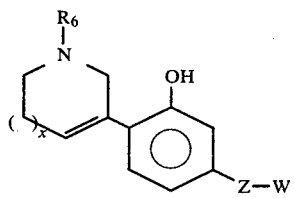

wherein x, Z and W are as defined in Example 3 and $R_6$ is:

| | | |
|---|---|---|
| CH$_2$C≡CH | (CH$_2$)$_4$C≡CH | (CH$_2$)$_3$—C≡C—CH$_3$ |
| (CH$_2$)$_2$C≡CH | CH(C$_3$H$_7$)—C≡CH | C≡CH |

EXAMPLE 22

3-[4-(1,1-Dimethylheptyl)-2-hydroxyphenyl]-1-N-(2-propenyl)piperidine

A mixture of 900 mg. (2.97 mmoles) of 3-[4-(1,1-dimethylheptyl)-2-hydroxyphenyl]piperidine, 481 mg. (3.48 mmoles) of anhydrous potassium carbonate and 359 mg. (2.97 mmoles) of allyl bromide in 20 ml. of ethanol is heated at reflux for 23 hours. The reaction mixture is concentrated under reduced pressure and the residue dissolved in 250 ml. of saturated sodium bicarbonate and 200 ml. of dichloromethane. The organic extract is washed once with 100 ml. of saturated sodium chloride, dried over magnesium sulfate and evaporated under reduced pressure to an oil. The oil is purified via column chromatography on 125 g. of silica gel eluted with 25% cyclohexane-ether to yield 172 mg. (15%) of 3-[4-(1,1-dimethylheptyl)-2-allyloxyphenyl]-1-N-(2-propenyl)-piperidine as an oil and 411 mg. (40%) of the title compound as an oil.

Title Compound

PMR: $\delta_{CDCl_3}{}^{TMS}$ 0.85 (m, terminal methyl), 1.25 (s, gem dimethyl), 3.1 (m, allyl methylene and C-2 or 6 methylene), 5.0–5.4 and 5.5–6.1 (m, three vinyl protons) and 6.8 (m, ArH).

IR: (CHCl$_3$) 1681, 1653, 1626 and 1597 cm$^{-1}$.

MS: m/e 343 (M+), 328, 316, 302, 259 and 258.

Neutralization of the title compound with ethanolic hydrogen chloride gives the hydrochloride salt as a glass.

Bis Allyl Compound

PMR: $\delta_{CDCl_3}{}^{TMS}$ 0.80 (m, terminal methyl), 1.22 (s, gem dimethyl), 2.98 and 3.10 (bs, allyl methylenes), 4.09 (dd, J=8 and 6 Hz, one H of C-2 methylene), 4.50 (dd, J=16 and 8 Hz, one H of C-2 methylene), 4.9–5.4 and 5.5–6.1 (m, six vinyl protons), 6.69 (d, J=2 Hz, ArH), 6.71 (dd, J=8 and 2 Hz, ArH) and 7.00 (d, J=8 Hz, ArH).

IR: (CHCl$_3$) 3521, 3226, 1653, 1629 and 1565 cm$^{-1}$.

MS: m/e 383 (M+), 368, 342, 298 and 257.

EXAMPLE 23

3-[4-(1,1-Dimethylheptyl)-2-hydroxyphenyl]-1-N-(2-propenyl)-1,2,5,6-tetrahydropyridine A mixture of 1.0 g. (3.32 mmoles) of 3-[4-(1,1-dimethylheptyl)-2-hydroxyphenyl]-1,2,5,6-tetrahydropyridine, 539 mg. (3.90 mmoles) of anhydrous potassium carbonate and 401 mg. (3.32 mmoles) of allyl bromide in 23 ml. of ethanol is heated at reflux for 23 hours. The reaction mixture is concentrated under reduced pressure and the residue dissolved in 250 ml. of saturated sodium bicarbonate and 200 ml. of dichloromethane. The organic extract is washed once with 100 ml. of saturated sodium chloride, dried over magnesium sulfate and evaporated to an oil. The oil is purified via column chromatography on 125 g. of silica gel eluted with 5% methanol-dichloromethane to yield 372 mg. (29%) of 3-[4-(1,1-dimethylheptyl)-2-allyloxyphenyl]-1-N-(2-propenyl)-1,2,5,6-tetrahydropyridine as an oil and 247 mg. (22%) of the title compound, M.P. 109°–110° C. (from ether-pentane).

Title Compound

PMR: $\delta_{CDCl_3}{}^{TMS}$ 0.85 (m, terminal methyl), 1.25 (s, gem dimethyl), 3.23 (m, allyl methylene), 5.0–5.4 and 5.5–6.1 (m, four vinyl protons), 6.82 (m, ArH) and 6.97 (d, J=8 Hz, ArH).

IR: (CHCl$_3$) 3425, 1631 and 1572 cm$^{-1}$.

MS: m/e 341 (M+), 326, 300, 272 and 256.

Neutralization of the title compound with ethanolic hydrogen chloride gives the hydrogen chloride salt as a glass.

Bis Allyl Compound

PMR: $\delta_{CDCL_3}{}^{TMS}$ 0.82 (terminal methyl), 1.25 (s, gem dimethyl), 3.03 and 3.12 (two m, allyl methylenes), 3.9–5.4 and 5.5–6.1 (m, seven vinyl protons), 6.71 (d, J=2 Hz, ArH), 6.72 (dd, J=8 and 2 Hz, ArH) and 7.13 (d, J=8 Hz, ArH).

IR: (CHCl$_3$) 3521, 3215, 1653, 1629 and 1565 cm$^{-1}$.

MS: m/e 381 (M+), 366, 340, 312, 284, 271 and 260.

EXAMPLE 24

1-N-Cyclopropylmethyl-3-[4-(1,1-dimethylheptyl)-2-hydroxyphenyl]-1,2,5,6-tetrahydropyridine To a solution of 596 mg. (1.98 mmoles) of 3-[4-(1,1-dimethylheptyl)-2-hydroxyphenyl]-1,2,5,6-tetrahydropyridine in 2.25 ml. of toluene and 4.5 ml. of pyridine is added 180 μl (3.96 mmoles) of cyclopropanecarboxylic acid chloride in 2.25 ml. of toluene. The reaction mixture is stirred for one hour at 25° C. and for 0.5 hour at 80° C. Another 180 μl (3.96 mmoles) portion of cyclopropanecarboxylic acid chloride is added and the heating at 80° C. continued for 2 hours. The reaction mixture is cooled and added to 300 ml. of saturated sodium chloride. The quenched mixture is extracted with two 75 ml. portions of dichloromethane. The extract is washed once with 50 ml. of saturated sodium chloride, dried over magnesium sulfate and evaporated to yield an oil. A solution of this oil in 100 ml. of ether is added dropwise to a mixture of 3.0 g. (78.9 mmoles) of lithium aluminum hydride in 150 ml. of ether. The reaction mixture is refluxed for 17 hours, cooled in ice and decomposed by the addition of 3 ml. of water, 3 ml. of 15% sodium hydroxide and 9 ml. more of water. After stirring for 30 minutes at 25° C. the quenched reaction mixture is filtered and the filtrate evaporated to a solid. Recrystallization from dichloromethane and pentane gives 296 mg. (42%) of the title compound.

MP: 118° C.

PMR: $\delta_{CDCl_3}^{TMS}$ 0.2 and 0.5 (m, cyclopropane), 0.84 (m, terminal methyl), 1.28 (s, gem dimethyl), 2.40 (m, C-5 or 6 and C-1 methylene), 2.75 (t, J=6 Hz, C-5 or 6 methylene), 3.26 (m, C-2 methylene), 5.80 (m, vinyl H), 6.75 (m, two ArH) and 6.96 (d, J=8 Hz, ArH).

MS: m/e 355 (M+), 340, 314, 300 and 270.

Neutralization of the title compound in ether with ethanolic hydrogen chloride gives the hydrochloride salt of the title compound as a foam.

In a similar manner the following compounds were prepared:

1-N-Cyclopropylmethyl-3-[4-(1,1-dimethylheptyl)-2-hydroxyphenyl]-piperidine as an oil (515 mg., 73%) from 3-[4-(1,1-dimethylheptyl)-2-hydroxyphenyl]-piperidine (600 mg., 1.98 mmoles) and cyclopropane carboxylic acid chloride (360 μl, 7.82 mmoles).

PMR: $\delta_{CDCl_3}^{TMS}$ 0.25 and 0.55 (m, cyclopropane), 0.82 (terminal methyl), 1.25 (s, gem dimethyl), 2.39 (d, J=6 Hz, C-1 methylene), 6.61 (dd, J=8 and 2 Hz, ArH), 6.79 (d, J=2 Hz, ArH) and 6.95 (d, J=8 Hz, ArH).

IR: (CHCl$_3$) 1639 and 1580 cm$^{-1}$.

MS: m/e 357, 342, 316, 302 and 273.

Neutralization of the title compound in ether with ethanolic hydrogen chloride gives the hydrochloride salt of the title compound as a foam.

1-N-Cyclobutylmethyl-3-[4-(1,1-dimethylheptyl)-2-hydroxyphenyl]-1,2,5,6-tetrahydropyridine (198 mg., 39%) from 3-[4-(1,1-dimethylheptyl)-2-hydroxyphenyl]-1,2,5,6-tetrahydropyridine (412 mg., 1.37 mmoles) and cyclobutane carboxylic acid chloride (586 μl, 5.48 mmoles).

MP: 116°-117° C. (from dichloromethane-pentane).

PMR: $\delta_{CDCl_3}^{TMS}$ 0.85 (m, terminal methyl), 1.25 (s, gem dimethyl), 2.40 and 2.80 (m, C-5, 6 and 1 methylenes), 3.48 (bs, C-2 methylene), 5.90 (m, vinyl H), 6.82 (m, ArH) and 7.02 (d, J=8 Hz, ArH).

IR: (CHCl$_3$) 3571, 3279, 1634 and 1572 cm$^{-1}$.

MS: m/e 369 (M+), 354, 314, 300 and 284.

Neutralization of the title compound in ether with ethanolic hydrogen chloride affords the hydrochloride salt of the title compound as a foam. 1-N-Cyclobutylmethyl-3-[4-(1,1-dimethylheptyl)-2-hydroxyphenyl]-piperidine as an oil (427 mg., 86%) from 3-[4-(1,1-dimethylheptyl)-2-hydroxyphenyl]piperidine (415 mg., 1.37 mmoles) and cyclobutanecarboxylic acid chloride (586 μl, 5.48 mmoles).

PMR: $\delta_{CDCl_3}^{TMS}$ 0.82 (m, terminal methyl), 1.25 (s, gem dimethyl), 6.60 (dd, J=8 and 2 Hz, ArH), 6.76 (d, J=2 Hz, ArH) and 6.82 (d, J=8 Hz, ArH).

IR: (CHCl$_3$) 1637 and 1575 cm$^{-1}$.

MS: m/e 371 (M+), 356, 316 and 302.

Neutralization of the title compound in ether with ethanolic hydrogen chloride produces the hydrochloride salt of the title compound as a foam.

EXAMPLE 25

1-Acetyl-3-[2-acetoxy-4-(1,1-dimethylheptyl)phenyl]-piperidine

To a solution of 2.0 g. of 3-[4-(1,1-dimethylheptyl)-2-hydroxyphenyl]-piperidine in 20 ml. of pyridine at 10° C. is added 20 ml. of acetic anhydride and the mixture stirred under nitrogen for 18 hours. It is then poured onto ice/water and acidified with dilute hydrochloric acid. The product is isolated by extraction with ethyl acetate (2×100 ml.). The combined extracts are washed with brine, dried (MgSO$_4$) and evaporated to give the product as an oil.

In like manner, the compounds of formulae I and II wherein $R_6$ is hydrogen and $R_1$ is hydrogen are converted to their diacyl derivatives. Replacement of acetic anhydride by propionic, butyric or valeric acid anyhydrides affords the corresponding diacyl derivatives.

When $R_6$ is other than hydrogen, the above procedure produces the monoacyl derivative of the phenolic hydroxy group.

EXAMPLE 26

3-[2-(4-Morpholinobutyryloxy)-4-(1,1-dimethylheptyl)-phenyl]-piperidine

Dicyclohexylcarbodiimide (0.227 g., 1.1 mmole) and 4-N-piperidyl-butyric acid hydrochloride (0.222 g., 1.0 mmole) are added to a solution of 3-[4-(1,1-dimethylheptyl)-2-hydroxyphenyl]piperidine (0.303 g., 1.0 mmole) in methylene chloride (25 ml.) at room temperature. The mixture is stirred for 18 hours and is then cooled to 0° C. and filtered. Evaporation of the filtrate affords the title product as its hydrochloride salt.

Similarly, the reactant of this example and the remaining phenolic compounds of this invention are converted to the basic esters of the phenolic hydroxy group by reaction with the appropriate basic acid reagent. Esters wherein the $R_1$ moiety has the following values are thus prepared:

—COCH$_2$NH$_2$

—CO(CH$_2$)$_2$N(C$_4$H$_9$)$_2$

—CO(CH$_2$)$_2$—N—(methyl)piperazino

—COC(CH$_3$)$_2$(CH$_2$)$_2$—piperidino

—CO(CH$_2$)$_3$N(C$_2$H$_5$)$_2$

—COCH(CH$_3$)(CH$_2$)$_2$—morpholino

—CO(CH$_2$)$_3$—pyrrolo

—CO(CH$_2$)$_3$—pyrrolidino

—COCH$_2$—pyrrolo

—CO(CH$_2$)$_3$—piperidino

—CO(CH$_2$)$_4$NH$_2$

—CO(CH$_2$)$_3$NH(C$_3$H$_7$)

—CO(CH$_2$)$_2$—N—butylpiperazino

Careful neutralization of the hydrochloride salts affords the free basic esters which are converted to other acid addition salts according to the procedure of Example 18. In this manner, the hydrobromide, sulfate, acetate, malonate, citrate, glycolate, gluconate, succinate, sulfosalicylate and tartrate salts are prepared.

EXAMPLE 27

General Hydrochloride Salt Formation

Excess hydrogen chloride is passed into a solution of the appropriate compound of formulae I-II and the resulting precipitate separated and recrystallized from an appropriate solvent, e.g. methanol-ether (1:10).

The remaining compounds of formulae I-II are converted to their hydrochlorides in like manner.

Similarly, the hydrobromide, sulfate, nitrate, phosphate, acetate, butyrate, citrate, malonate, maleate, fumarate, malate, glycolate, gluconate, lactate, salicylate, sulfosalicylate, succinate, pamoate, tartrate and embonate salts are prepared.

EXAMPLE 28

3-[4-(1,1-Dimethylheptyl)-2-hydroxyphenyl]piperidine 2'-O-hemisuccinate Ester Sodium Salt To a 0° C. solution of 0.606 g. (2.0 mmoles) of 3-[4-(1,1-dimethylheptyl)-2-hydroxyphenyl]piperidine in 3 ml. of dichloromethane is added 0.244 g. (2.0 mmoles) of 4-N,N-dimethylaminopyridine. To the resultant solution is slowly added 0.200 g. (2.0 mmoles) of succinic anhydride in one ml. of dichloromethane. The reaction mixture is stirred for 4 hours at 0° C. and then 2.00 ml. of 1 N hydrochloric acid is slowly added. The reaction mixture is stirred 5 minutes longer and then added to 100 ml. water-100 ml. dichloromethane. The dichloromethane extract is dried over magnesium sulfate and evaporated. The residue is dissolved in 5 ml. of ethanol and 2.00 ml. of 1 N sodium hydroxide in ethanol added. Addition of ether causes crystallization. Recrystallization from ethanol-ether yields the title compound.

Replacement of sodium hydroxide by potassium hydroxide in the above procedure affords the potassium salt.

By means of this procedure, the remaining compounds described herein are converted to their hemisuccinate esters.

EXAMPLE 29

3-[4-(1,1-Dimethylheptyl)-2-hydroxyphenyl]piperidine 2'-O-Phosphate Ester Monosodium Salt To a 0° C. slurry of 0.126 g. (3.14 mmoles) of potassium hydride in 3 ml. of dimethylformamide is added a solution of 0.953 g. (3.14 mmoles) of 3-[4-(1,1-dimethylheptyl)-2-hydroxyphenyl]piperidine in 3 ml. of dimethylformamide. After gas evolution ceases (~10 min.) 0.932 g. (3.14 mmoles) of dibenzylphosphochlridate is slowly added. The reaction mixture is stirred for one hour and then added to 200 ml. ether-100 ml. water. The ether extract is washed with two 100 ml. portions of water, dried over magnesium sulfate and evaporated to a residue. The residue is mixed with 1.0 g. of 5% platinum on carbon and 25 ml. of ethanol and stirred under one atmosphere of hydrogen for 3 hours. The reaction mixture is filtered through diatomaceous earth and 3.14 ml. of 1 N sodium hydroxide in ethanol slowly added to the filtrate. Addition of ether causes crystallization of the product. Recrystallization from ethanol then yields the title compound.

Similarly, the remaining compounds described herein are converted to their phosphate ester monosodium salts and, by replacement of sodium hydroxide with potassium hydroxide, to their corresponding potassium salts.

EXAMPLE 30

One hundred mg. of 3-[4-(1,1-dimethylheptyl)-2-hydroxyphenyl]piperidine are intimately mixed and ground with 900 mg. of starch. The mixture is then loaded into telescoping gelatine capsules such that each capsule contains 10 mg. of drug and 90 mg. of starch.

EXAMPLE 31

A tablet base is prepared by blending the ingredients listed below:
Sucrose—80.3 parts
Tapioca starch—13.2 parts
Magnesium stearate—6.5 parts Sufficient 1-benzyl-3-[2-benzyloxy-4-(1,1-dimethylheptyl)phenyl]-1,2,5,6-tetrahydropyridine is blended into this base to provide tablets containing 0.1, 0.5, 1, 5, 10 and 25 mg. of drug.

EXAMPLE 32

Suspensions of 1-benzyl-3-[4-(1,1-dimethylheptyl)-2-hydroxyphenyl]1,2,5,6-tetrahydropyridine are prepared by adding sufficient amounts of drug to 0.5% methylcellulose to provide suspensions having 0.05, 0.1, 0.5, 1, 5 and 10 mg. of drug per ml.

PREPARATION A 2-(3-Benzyloxyphenyl)-2-methylpropionitrile

In a solution of 1500 ml. of dimethylsulfoxide saturated with methyl bromide is simultaneously added a solution of 294 g. (1.32 mole) of 2-(3-benzyloxyphenyl)acetonitrile in 200 ml. dimethyl sulfoxide and a solution of 420 ml. of 50% aqueous sodium hydroxide. Methyl bromide is continuously bubbled through the reaction mixture during the above addition (30 minutes) and then for 1.5 hours longer while the reaction temperature is maintained at ≦50° C. with ice cooling. The reaction mixture is added to 2 liters of water-2 kg. ice and the resultant mixture extracted four times with 1 liter of ether. The combined ether extracts are washed twice with one liter of water, once with one liter of saturated sodium chloride, dried over magnesium sulfate and evaporated to yield 325 g. (98%) of product as an oil.

PMR: $\delta_{CDCl_3}^{TMS}$ 1.70 (s, methyl), 5.12 (s, methylene), 6.8–7.5 (m, ArH) and 7.45 (s, PhH).

IR: (CHCl$_3$) 2247, 1616 and 1603 cm$^{-1}$.

MS: m/e 251 (M+), 236, 160 and 91.

PREPARATION B 2-(3-Benzyloxyphenyl)-2-methylpropionaldehyde

To a 15° C. solution of 325 g. (1.25 mole) of 2-(3-benzyloxyphenyl)-2-methylpropionitrile in 1.85 liters of tetrahydrofuran is added 1.6 moles of diisobutylaluminum hydride as a 1.3 M solution in hexane (reaction temperature is maintained at 15°–18° C.). The reaction mixture is allowed to warm to room temperature and is stirred 2 hours longer. It is then quenched be addition to a solution of 170 ml. of concentrated sulfuric acid in 670 ml. of water (temperature ≦30° C.). The resultant mixture is allowed to warm to room temperature and is then stirred an additional 2 hours. The organic layer is separated and the aqueous phase extracted once with one liter of ether. The combined organic phase is washed with 500 ml. of water and 500 ml. of saturated sodium chloride, dried over magnesium sulfate and evaporated to yield 315 g. (99%) of the title product.

PMR: $\delta_{CDCl_3}{}^{TMS}$ 1.43 (s, methyls), 5.08 (s, methylenes), 6.8–7.5 (m, ArH), 7.4 (s, PhH) and 9.55 (s, aldehyde).

PREPARATION C 2-(3-Benzyloxyphenyl)-2-methyl-cis-oct-3-ene

To a 15° C. solution of 1.8 moles of dimsyl sodium (from sodium hydride and dimethyl sulfoxide) in 2 liters of dimethyl sulfoxide is added, portionwise, 768 g. (1.8 moles) of pentyltriphenylphosphonium bromide. The resultant slurry is stirred 15 minutes at 15°–20° C. and then 3.5 g. (1.24 moles) of 2-(3-benzyloxyphenyl)-2-methylpropionaldehyde is slowly added (reaction temperature $\leq$30° C.). The resultant mixture is stirred for 4 hours at room temperature and is then added to 6 liters of ice water. The quenched reaction is extracted four times with one liter portions of 50% ether-pentane. The combined extract is washed twice with one liter of water and once with one liter of saturated sodium chloride and is then dried over magnesium sulfate and evaporated to yield an oil. Crystallization of this oil in 50% ether-pentane (to remove triphenylphosphine oxide), filtration and evaporation of the filtrate gives 559 g. of oil. The crude oil is purified via column chromatography on 2 kg. of silica gel eluted with 20% hexane-dichloromethane to yield 217 g. (57%) of 2-(3-benzyloxyphenyl)-2-methyl-cis-oct-3-ene.

PMR: $\delta_{CDCl_3}{}^{TMS}$ 0.75 (bt, J=6 Hz, terminal methyl), 1.1 (m, two sidechain methylenes), 1.43 (s, gem dimethyl), 1.60 (m, allylic methylene), 5.09 (s, benzylic methylene, 5.28 (dt, J=12 and 6 Hz, vinyl H), 5.70 (dd, J=12 and 1 Hz, vinyl H), 6.7–7.5 (m, ArH) and 7.42 (s, PhH).

IR: (CHCl$_3$) 1610 and 1587 cm$^{-1}$.

MS: m/e 308 (M+), 293, 274, 265, 251, 239, 225, 217 and 91.

Similarly, 1-benzyloxy-3-(1,1-dimethyloct-2-enyl)-benzene (13.5 g., 70%) is prepared from 15.75 g. (0.062 mol.) of 2-(3-benzyloxyphenyl)-2-methylpropionaldehyde and 37.5 g. (0.0899 mol.) of hexyltriphenylphosphonium bromide. The product is an oil.

PMR: $\delta_{CDCl_3}{}^{TMS}$ 0.78 (m, terminal sidechain methyl), 1.40 (s, gem dimethyl), 4.97 (s, benzyl ether methylene), 5.23 (m, vinyl H), 5.57 (d, J=11 Hz, vinyl H) and 6.6–7.4 (m, ArH and PhH).

IR: (CHCl$_3$) 1608 and 1582 cm$^{-1}$.

MS: m/e 322 (M+), 307, 279, 274, 265 and 231.

PREPARATION D 2-(3-Hydroxyphenyl)-2-methyloctane

A mixture of 65 g. (0.211 mole) of 2-(3-benzyloxyphenyl)-2-methyl-cis-oct-3-ene and 7.5 g. of 10% palladium-on-carbon in 100 ml. of ethanol is hydrogenated for one hour on a Parr apparatus at 50 p.s.i. hydrogen pressure. Additional 7.5 g. portions of 10% palladium-on-carbon are added after one and two hours of reaction and the reaction continued for 12 more hours. The reaction mixture is filtered through diatomaceous earth with ethanol and the filtrate evaporated to an oil. The oil is purified via column chromatography on one kg. of silica gel eluted with 50% hexane-dichloromethane to yield 105 g. (78%) of 2-(3-hydroxyphenyl)-2-methyloctane.

PMR: $\delta_{CDCl_3}{}^{TMS}$ 0.85 (bt,terminal methyl), 1–1.9 (m, methylenes), 1.29 (s, gem dimethyl), 4.98 (s, phenol H) and 6.6–7.4 (m, ArH).

IR: (CHCl$_3$) 3571, 3311 and 1592 cm$^{-1}$.

MS: m/e 220 (M+), 205 and 135.

In like manner, 2-(3-hydroxyphenyl)-2-methylnonane is prepared in 82% (7.8 g.) yield from 13.0 (0.0406 mol.) of 1-benzyloxy-3-(1,1-dimethyl-oct-2-enyl)benzene. It is obtained as an oil having the characteristics:

PMR: $\delta_{CDCl_3}{}^{TMS}$ 0.85 (m, terminal methyl), 1.27 (s, gem dimethyl), 5.25 (bs, OH) and 6.6–7.4 (m, ArH).

IR: (CHCl$_3$) 3571, 3279, 1563 and 1527 cm$^{-1}$.

MS: m/e 234 (M+), 219, 191, 178, 164, 149, 135 and 121.

PREPARATION E 2-(4-Bromo-3-hydroxyphenyl)-2-methyloctane

To a 0° C. solution of 110 g. (0.05 mole) of 2-(3-hydroxyphenyl)-2-methyloctane in 200 ml. of carbon tetrachloride is added dropwise a solution of 80 g. (0.50 mole) of bromine in 90 ml. of carbon tetrachloride (reaction temperature $\leq$30° C. with cooling). The reaction mixture is stirred an additional 15 minutes and is then evaporated to yield 150 g. (100%) of 2-(4-bromo-3-hydroxyphenyl)-2-methyloctane.

PMR: $\delta_{CDCl_3}{}^{TMS}$ 0.85 (bt, terminal methyl), 0.8–1.9 (m, methylenes), 1.28 (s, gem dimethyl), 5.4 (bs, phenolic H), 6.78 (dd, J=8 and 2 Hz, C-6 ArH), 7.02 (d, J=2 Hz, C-2 ArH) and 7.37 (d, J=8 Hz, C-5 ArH).

In like manner, 2-(4-bromo-3-hydroxyphenyl)-2-methylnonane is prepared in 82% (8.5 g.) yield as an oil from 7.8 g. (0.033 mol.) of 2-(3-hydroxyphenyl)-2-methylnonane:

PMR: $\delta_{CDCl_3}{}^{TMS}$ 0.86 (m, terminal methyl), 1.27 (s, gem dimethyl), 5.50 (bs, OH), 6.83 (dd, J=8 and 2 Hz, ArH), 7.08 (d, J=2 Hz, ArH) and 7.43 (d, J=8 Hz, ArH).

IR: (CHCl$_3$) 3279, 1613 and 1587 cm$^{-1}$.

MS: m/e 314, 312 (M+), 212, 210, 185 and 187.

PREPARATION F 2-(3-Benzyloxy-4-bromophenyl)-2-methyloctane

To a −18° C. slurry of 23.0 g. (0.575 mole) of potassium hydride in 400 ml. of N,N-dimethylformamide is added over a 45 minute period a solution of 150 g. (0.5 mole) of 2-(4-bromo-3-hydroxyphenyl)-2-methyloctane in 400 ml. of N,N-dimethylformamide (reaction temperature $\leq$ −15° C.). The reaction mixture is stirred 15 minutes longer after which a solution of 98.3 g. (0.575 mole) of benzyl bromide in 200 ml. of N,N-dimethylformamide is added. The mixture is then warmed to room temperature and stirred 30 minutes longer. It is quenched by addition to 6 liters of ice water. The quenched mixture is extracted six times with 500 ml. of ether. The combined extract is washed twice with one liter portions of water and once with one liter of saturated sodium chloride, dried over magnesium sulfate and evaporated to a quantitative yield of the title product.

PMR: $\delta_{CDCl_3}{}^{TMS}$ 0.85 (bt, terminal methyl), 0.8–2.0 (m, methylenes), 1.22 (s, gem dimethyl), 5.17 (s, benzylic methylene) and 6.7–7.6 (two multiplets, ArH and PhH).

IR: (CHCl$_3$) 1592 and 1575 cm$^{-1}$.

MS: m/e 390, 388 (M+), 375, 373, 354, 352, 305, 303 and 91.

And, 2-(3-benzyloxy-4-bromophenyl)-2-methylnonane is prepared in 95% (10.4 g.) yield from 2-(3-hydroxy-4-bromophenyl)-2-methylnonane (8.5 g., 0.027 mol.), sodium hydried (0.744 g., 0.031 mol.) and benzyl bromide (5.3 g., 0.031 mol.) as an oil.

PMR: $\delta_{CDCl_3}^{TMS}$ 0.87 (terminal methyl), 1.23 (s, gem dimethyl), 5.18 (s, benzyl ether methylene, 6.8 (dd, J=8 and 2 Hz, ArH), 6.97 (d, J=2 Hz, ArH) and 7.43 (m, ArH and PhH).

IR: (CHCl$_3$) 1600 and 1575 cm$^{-1}$.

MS: m/e 404, 402 (M+), 305, 303, 91.

The compounds tabulated below are prepared according to the procedures of Preparations C-F from appropriate reactants:

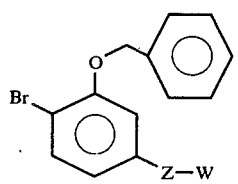

| Z | W |
|---|---|
| C(CH$_3$)$_2$(CH$_2$)$_2$ | H |
| C(CH$_3$)$_2$(CH$_2$)$_{10}$ | H |
| C(CH$_3$)$_2$(CH$_2$)$_4$ | C$_6$H$_5$ |
| C(CH$_3$)$_2$(CH$_2$)$_4$ | 4-pyridyl |
| C(CH$_3$)$_2$(CH$_2$)$_3$ | 2-pyridyl |
| C(CH$_3$)$_2$(CH$_2$)$_{10}$ | C$_6$H$_5$ |
| CH(CH$_3$)(CH$_2$)$_2$ | C$_6$H$_5$ |
| CH(C$_2$H$_5$)(CH$_2$)$_2$ | 4-ClC$_6$H$_4$ |
| CH(C$_2$H$_5$)(CH$_2$)$_4$ | 4-FC$_6$H$_4$ |
| (CH$_2$)$_5$ | H |
| (CH$_2$)$_{11}$ | H |
| (CH$_2$)$_{13}$ | H |
| (CH$_2$)$_4$ | C$_6$H$_5$ |
| (CH$_2$)$_8$ | H |

PREPARATION G

3-Benzyloxy-4-bromophenol

To a 0° C. slurry of 1.7 g. (42.5 mmoles) of potassium hydride in 35 ml. of N,N-dimethylformamide is slowly added a solution of 7.22 g. (38.2 mmoles) of 4-bromoresorcinol. The resultant mixture is stirred for 30 minutes and then 4.54 ml. (38.2 mmoles) of benzyl bromide is slowly added. The reaction mixture is stirred 3 hours longer at 0° C. and then added to 200 ml. of cold water and 200 ml. of ether. The ether extract is washed twice with 200 ml. portions of water, dried over magnesium sulfate and evaporated to an oil. The crude oil is purified via column chromatography on 400 g. of silica gel eluted with 25% ether-pentane to yield (in order of elution) 2.2 g. (16%) of 2,4-dibenzyloxybromobenzene, 0.21 g. (2%) of 5-benzyloxy-2-bromophenol and 3.52 g. (33%) of 3-benzyloxy-4-bromophenol.

5-Benzyloxy-2-bromophenol

PMR: $\delta_{CDCl_3}^{TMS}$ 4.98 (s, benzyl ether), 5.46 (bs, OH), 6.40 (dd, J=8 and 2 Hz, ArH), 6.60 (d, J=2 Hz, ArH), 7.17 (d, J=8 Hz, ArH) and 7.33 (s, PhH).

IR: (CHCl$_3$) 3521, 3221, 1610 and 1600 cm$^{-1}$.

MS: m/e 280, 278 (M+), 189, 187 and 91.

3-Benzyloxy-4-bromophenol

PMR: $\delta_{CDCl_3}^{TMS}$ 5.00 (s, benzyl ether methylene, 5.33 (bs, OH), 6.21 (dd, J=8 and 2 Hz, ArH), 6.38 (d, J=2 Hz, ArH) and 7.30 (m, ArH and PhH).

IR: (CHCl$_3$) 3546, 3257, 1603 and 1585 cm$^{-1}$.

MS: m/e 280, 278 (M+) and 91.

PREPARATION H

2-Benzyloxy-4-[2-(5-phenylpentyloxy)]bromobenzene

A mixture of 3.50 g. (12.5 mmoles) of 3-benzyloxy-4-bromophenol, 3.48 g. (14.4 mmoles) of 2-(5-phenylpentyl)methanesulfonate and 5.17 g. (37.5 mmoles) of anhydrous potassium carbonate in 20 ml. of N,N-dimethylformamide is heated at 85° C. for 6 hours. It is then cooled and added to 200 ml. of water and 200 ml. of ether. The organic extract is washed twice with 150 ml. portions of water, dried over magnesium sulfate and evaporated to an oil. The oil is purified via column chromatography on 400 g. of silica gel eluted with 2:1 pentane:methylene chloride to yield 4.39 g. (82%) of the desired product as an oil.

PMR: $\delta_{CDCl_3}^{TMS}$ 1.21 (d, J=6 Hz, sidechain methyl), 1.7 (m, sidechain methylenes), 2.60 (m, sidechain benzyl methylene), 4.25 (m, sidechain methine), 5.00 (s, benzyl ether methylene), 6.22 (dd, J=8 and 2 Hz, C-5 ArH), 6.39 (d, J=2 Hz, C-3 ArH) and 7.30 (m, PhH and C-6 ArH).

IR: (CHCl$_3$) 1587 cm$^{-1}$.

MS: 426, 424 (M+), 280, 278 and 91.

The following compounds are similarly prepared from the appropriate mesylate CH$_3$SO$_3$-Z-W.

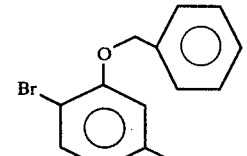

| (alk$_2$) | W |
|---|---|
| (CH$_2$)$_4$ | 4-FC$_6$H$_4$ |
| (CH$_2$)$_8$ | C$_6$H$_5$ |
| (CH$_2$)$_{10}$ | 4-ClC$_6$H$_4$ |
| CH(CH$_3$)(CH$_2$)$_8$ | C$_6$H$_5$ |
| CH(CH$_3$)CH$_2$ | 4-FC$_6$H$_4$ |
| C(CH$_3$)$_2$(CH$_2$)$_3$ | C$_6$H$_5$ |
| CH$_2$CH(CH$_3$)CH$_2$ | C$_6$H$_5$ |
| CH(CH$_3$)(CH$_2$)$_{10}$ | H |
| C(CH$_3$)$_2$(CH$_2$)$_5$ | H |
| C(CH$_3$)$_2$(CH$_2$)$_7$ | H |
| (CH$_2$)$_{13}$ | H |
| (CH$_2$)$_{13}$ | C$_6$H$_5$ |
| CH(CH$_3$)(CH$_2$)$_6$ | 4-FC$_6$H$_4$ |
| C(CH$_3$)$_2$(CH$_2$)$_{10}$ | 4-FC$_6$H$_4$ |
| (CH$_2$)$_{12}$ | C$_6$H$_5$ |
| CH(C$_2$H$_5$)(CH$_2$)$_3$ | 4-ClC$_6$H$_4$ |
| C(CH$_3$)$_2$(CH$_2$)$_3$ | H |
| (CH$_2$)$_2$C(CH$_3$)$_2$(CH$_2$)$_2$ | H |
| (CH$_2$)$_6$ | C$_6$H$_5$ |
| (CH$_2$)$_{12}$ | H |
| CH(CH$_3$)(CH$_2$)$_3$ | 4-pyridyl |
| (CH$_2$)$_2$ | 4-pyridyl |
| CH(CH$_3$)(CH$_2$)$_3$ | 2-pyridyl |
| (CH$_2$)$_5$ | 3-pyridyl |
| (CH$_2$)$_{10}$ | 2-pyridyl |
| CH(C$_2$H$_5$)(CH$_2$)$_2$ | 4-pyridyl |

PREPARATION I

3-(3-Benzyloxy)benzyloxypropane

Sodium (0.2 mole) is dissolved in n-propylalcohol (1.0 mole) and the reaction mixture then cooled in an ice-bath. Then 0.2 mole of 3-benzyloxybenzyl chloride is added with constant stirring over a half-hour period. The ice-bath is removed and the temperature gradually raised to reflux. After 4 hours at reflux, the excess alcohol is removed by distillation under reduced pressure. The residue is treated with water to dissolve the salt present and then extracted with diethyl ether. The extract is washed with water, dried (MgSO$_4$) and evaporated to give the title product.

In those instances where the alcohol reactant is not readily available or is a solid at normal temperatures, a modification of this procedure is used. The appropriate alcohol is dissolved in acetone and heated with the halide reactant in the presence of powdered potassium carbonate for 6–8 hours. The reaction mixture is then cooled, water added and the ether recovered as described above.

The following compounds are prepared in like manner from appropriate alcohols:

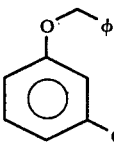

| (alk$_2$) | W | (alk$_2$) | W |
|---|---|---|---|
| (CH$_2$)$_2$ | H | — | C$_6$H$_5$ |
| (CH$_2$)$_4$ | H | — | 4-pyridyl |
| (CH$_2$)$_{12}$ | H | CH(CH$_3$)(CH$_2$)$_2$ | C$_6$H$_5$ |
| (CH$_2$) | C$_6$H$_5$ | CH$_2$ | C$_6$H$_5$ |
| CH(CH$_3$)CH$_2$ | H | (CH$_2$)$_5$ | 4-FC$_6$H$_4$ |
| (CH$_2$)$_2$CH(CH$_3$) | C$_6$H$_5$ | CH$_2$CH(C$_2$H$_5$)CH$_2$ | H |

Bromination of the ethers according to the method of Preparation E affords the corresponding 2-bromo-5-(Z-W substituted)phenol benzyl ethers.

PREPARATION J

2-(3-Methoxyphenyl)-5-phenylpentane

A solution of 1-bromopropylbenzene (51.7 g.) in ether (234 ml.) is added dropwise over a 2-hour period to a refluxing mixture of magnesium (7.32 g.) in ether (78 ml.). The reaction mixture is refluxed for 30 minutes longer and then a solution of 3-methoxy-acetophenone (41.6 g.) in ether (78 ml.) is added dropwise and the mixture heated to reflux for 1.5 hours. The reaction is quenched by addition of saturated ammonium chloride (234 ml.), the ether layer is separated and the aqueous phase extracted with ether (3×200 ml.). The combined ether extracts are dried over magnesium sulfate and concentrated under vacuum to yield an oil. The oil is hydrogenated in a mixture containing ethanol (300 ml.), concentrated hydrochloric acid (2 ml.) and 5% palladium-on-carbon (5 g.). The catalyst is filtered off and the ethanol removed under vacuum. The residue is distilled under vacuum to give the title product.

PREPARATION K

2-(3-Hydroxyphenyl)-5-phenylpentane

A mixture of 2-(3-methoxyphenyl)-5-phenylpentane (18.4 g.) and pyridine hydrochloride (94 g.) under nitrogen is heated to 190° C. for 2 hours with vigorous stirring. The reaction mixture is cooled, dissolved in 6 N hydrochloric acid (200 ml.) and diluted with water to 600 ml. The aqueous solution is extracted with ethyl acetate (4×100 ml. ), the ethyl acetate extracts dried over sodium sulfate and concentrated under vacuum to yield the crude product. The product is purified by silica gel chromatography.

The following compounds are prepared from appropriate reactants by the method of Preparation J and that of the above preparation:

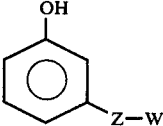

| Z | W |
|---|---|
| CH(CH$_3$)(CH$_2$)$_2$ | C$_6$H$_5$ |
| CH(C$_2$H$_5$)(CH$_2$)$_2$ | 4-ClC$_6$H$_4$ |
| CH(C$_2$H$_5$)(CH$_2$)$_4$ | 4-FC$_6$H$_4$ |
| (CH$_2$)$_5$ | H |
| (CH$_2$)$_{11}$ | H |
| (CH$_2$)$_{13}$ | H |
| (CH$_2$)$_4$ | C$_6$H$_5$ |
| (CH$_2$)$_8$ | H |

Bromination of the above compounds according to the procedure of Preparation E affords the corresponding 4-bromo derivatives, e.g. 2-(4-bromo-3-hydroxyphenyl)-5-phenylpentane.

PREPARATION L

Ethyl 3-(3-Benzyloxyphenyl)crotonate (Wittig Reaction)

A mixture of 3-benzyloxyacetophenone (29.4 g., 0.13 mole) and carbethoxymethylenetriphenylphosphorane (90.5 g., 0.26 mole) is heated under a nitrogen atmosphere at 170° C. for 4 hours. The clear melt is cooled to room temperature, triturated with ether and the precipitate of triphenyl phosphine oxide removed by filtration. The filtrate is concentrated under vacuum to an oily residue which is chromatographed over silica gel (1500 g.) and eluted with benzene:hexane solutions of increasing benzene concentration beginning with 40:60 and ending with 100% benzene. Concentration of appropriate fractions gives the product as an oily residue.

PREPARATION M

3-(3-Benzyloxyphenyl)butyl Tosylate

A solution of ethyl 3-(3-benzyloxyphenyl)crotonate (17.8 g., 60 mmole) in ether (250 ml.) is added to a mixture of lithium aluminum hydride (3.42 g., 90 mmole) and ether (250 ml.). Aluminum chloride (0.18 g., 1.35 mmole) is added and the mixture refluxed for 12 hours and then cooled. Water (3.4 ml.), sodium hydroxide (3.4 ml. of 6 N) and water (10 ml.) are then added successively to the reaction mixture. The inorganic salts which precipitate are filtered off and the filtrate is then concentrated in vacuo to give the 3-(3-benzyloxyphenyl)butanol as an oil.

Tosyl chloride (11.1 g., 58.1 mmole) is added to a solution of 3-(3-benzyloxyphenyl)-1-butanol (14.5 g., 57 mmole) in pyridine (90 ml.) at −45° C. The reaction mixture is held at −35° C. for 18 hours and is then diluted with cold 2 N hydrochloric acid (1500 ml.) and extracted with ether (5×200 ml.). The combined extracts are washed with saturated sodium chloride solution (4×250 ml.) and then dried (Na$_2$SO$_4$). Concentration of the dried extract affords the product as an oil.

PREPARATION N

3-(3-Benzyloxyphenyl)-1-phenoxybutane

A solution of phenol (4.56 g., 48.6 mmole) in dimethylformamide (40 ml.) is added under a nitrogen atmosphere to a suspension of sodium hydride (2.32 g., 48.6 mmole) of 50% (previously washed with pentane) in dimethylformamide (70 ml.) at 60° C. The reaction mixture is stirred for one hour at 60°-70° C., after which a solution of 3-(3-benzyloxyphenyl)butyl tosylate (18.9 g., 46 mmole) in dimethylformamide (80 ml.) is added. The reaction mixture is stirred at 80° C. for a half hour and is then cooled to room temperature, diluted with cold water (2500 ml.) and extracted with ether (4×400 ml.). The combined extracts are washed successively with cold 2 N hydrochloric acid (2×300 ml) and saturated sodium chloride solution (3×300 ml.) and then dried (Na$_2$SO$_4$). Removal of the solvent under reduced pressure affords the product as an oil. The oily residue is dissolved in benzene and filtered through silica gel (100 g.). Concentration of the filtrate under reduced pressure gives the product as an oil.

Repetition of Preparations L through N but using the 3-benzyloxy derivatives of benzaldehyde, acetophenone or propiophenone, the appropriate carbethoxy (or carbomethoxy) alkylidenetriphenylphosphorane, and the appropriate alcohol or phenol affords the following compounds.

(alk$_1$)—O—(alk$_2$)$_n$—W

| (alk$_1$) | n | (alk$_2$) | W |
|---|---|---|---|
| (CH$_2$)$_3$ | 1 | (CH$_2$)$_3$ | H |
| (CH$_2$)$_3$ | 1 | (CH$_2$)$_5$ | H |
| (CH$_2$)$_5$ | 1 | (CH$_2$)$_8$ | H |
| (CH$_2$)$_6$ | 1 | (CH$_2$)$_7$ | H |
| (CH$_2$)$_3$ | 1 | (CH$_2$)$_7$ | H |
| (CH$_2$)$_3$ | 1 | (CH$_2$)$_{10}$ | H |
| (CH$_2$)$_{10}$ | 1 | (CH$_2$)$_2$ | H |
| C(CH$_3$)$_2$(CH$_2$)$_2$ | 1 | (CH$_2$)$_4$ | H |
| (CH$_2$)$_4$ | 1 | CH$_2$ | C$_6$H$_5$ |
| (CH$_2$)$_6$ | 0 | — | C$_6$H$_5$ |
| (CH$_2$)$_{13}$ | 0 | — | H |
| (CH$_2$)$_6$ | 0 | — | H |
| (CH$_2$)$_6$ | 1 | CH$_2$ | 4-ClC$_6$H$_4$ |
| (CH$_2$)$_6$ | 0 | — | 4-FC$_6$H$_4$ |
| CH(CH$_3$)(CH$_2$)$_2$ | 0 | — | C$_6$H$_5$ |
| CH(CH$_3$)(CH$_2$)$_3$ | 0 | — | C$_6$H$_5$ |
| CH(CH$_3$)(CH$_2$)$_6$ | 0 | — | H |
| (CH$_2$)$_3$ | 0 | — | 4-pyridyl |
| (CH$_2$)$_3$ | 0 | — | 3-pyridyl |
| (CH$_2$)$_3$ | 1 | CH(CH$_3$) | 2-pyridyl |
| CH(CH$_3$)(CH$_2$)$_2$ | 1 | (CH$_2$)$_4$ | 4-pyridyl |
| CH(C$_2$H$_5$)(CH$_2$)$_2$ | 1 | CH(CH$_3$) | 2-pyridyl |
| (CH$_2$)$_4$ | 1 | (CH$_2$)$_5$ | 4-pyridyl |
| (CH$_2$)$_8$ | 1 | (CH$_2$)$_5$ | 4-pyridyl |

Bromination of the products according to the procedure of Preparation E affords the corresponding 2-bromo-5-[(alk$_1$)-O-(alk$_2$)$_n$-W]phenolbenzyl ethers.

PREPARATION O

4-(3-Hydroxyphenyl)-1-(4-pyridyl)pentane

A mixture of 3-(3-methoxyphenyl)butyl triphenylphosphonium bromide (17.5 g., 35.4 mmoles) in dimethylsulfoxide (50 ml.) is added to 4-pyridinecarboxaldehyde (3.79 g., 35.4 mmoles) in tetrahydrofuran (40 ml.). The resulting mixture is then added dropwise to a slurry of 50% sodium hydride (1.87 g., 39 mmoles) in tetrahydrofuran (20 ml.) under a nitrogen atmosphere at 0°-5° C. Following completion of addition, the mixture is stirred for one hour at 0°-5° C. and then concentrated under reduced pressure. The concentrate is diluted with water (200 ml.) and then acidified with 6 N HCl. The aqueous acid solution is extracted with benzene (4×50 ml.). It is then made basic and extracted with ethyl acetate (3×50 ml.). Evaporation of the combined extracts after drying (MgSO$_4$) affords 4-(3-methoxyphenyl)-1-(4-pyridyl)-1-pentene as an oil.

Catalytic hydrogenation of the thus-produced pentene derivative in ethanol at 45 p.s.i in the presence of Pd/C (1 g. of 10%) and concentrated HCl (1 ml.) affords the title product.

The pentene derivative thus obtained is demethylated by heating a mixture of the compound (25 mmoles) and pyridine hydrochloride (35 g.) under a nitrogen atmosphere at 210° C. for 8 hours. The hot mixture is poured into water (40 ml.) and the resulting solution made basic with 6 N sodium hydroxide. Water and pyridine are removed by distillation in vacuo. Ethanol (50 ml.) is added to the residue and the inorganic salts which precipitate are filtered off. The filtrate is concentrated in vacuo and the residue chromatographed on silica gel using as eluting agents 5% ethanol/benzene (4 liters), 10% ethanol/benzene (1 liter), 13% ethanol/benzene (1 liter) and 16% ethanol/benzene (5 liters). The product is isolated by concentration of appropriate fractions of the eluate.

The 3-(3-methoxyphenyl)butyltriphenylphosphonium bromide is prepared by refluxing a mixture of 1-bromo-3-(3-methoxyphenyl)butane (78.5 mmoles) and triphenyl phosphine (78.5 mmoles) in xylene (60 ml.) for 18 hours. The reaction mixture is then cooled to room temperature and filtered. The filter cake is washed with ether and the product dried in a vacuum desiccator.

Repetition of this procedure but using the appropriate bromo-(methoxyphenyl)alkane and the appropriate aldehyde or ketone affords the following compounds.

| Z | W |
|---|---|
| (CH$_2$)$_3$ | 2-pyridyl |
| (CH$_2$)$_4$ | 4-pyridyl |
| CH(CH$_3$)CH(CH$_3$)CH$_2$ | 3-pyridyl |
| CH(CH$_3$)CH(CH$_3$)CH$_2$ | 4-pyridyl |
| CH(C$_2$H$_5$) (CH$_2$)$_2$ | 4-pyridyl |
| (CH$_2$)$_{10}$ | 4-pyridyl |

Bromination of the above compounds according to the method of Preparation E gives the corresponding 2-bromo-5-(Z-W)-phenols.

PREPARATION P

3-Methoxy-α-methylstyrene Oxide

To a solution of dimethylsulfoxonium methylide (69.4 mmoles) in dimethyl sulfoxide (65 ml.) at room temperature is added solid 3-dimethoxyacetophenone (8.33 g., 55.5 mmoles). The reaction mixture is stirred for one hour at 25° C., for one-half hour at 50° C. and is then cooled. The mixture is diluted with water (50 ml.) and added to a mixture of ice water (200 ml.)—ether (250 ml.)—low boiling petroleum ether (25 ml.). The organic extract is washed twice with water (250 ml.), dried (MgSO$_4$) and evaporated to an oil which is fractionally distilled.

PREPARATION Q

2-(3-Methoxyphenyl)-2-hydroxypropyl-2-phenylethyl Ether

A mixture of dry 2-phenylethanol (30 ml., 251 mmoles) and sodium metal (690 mg., 30 mmoles) is heated at 110° C. for 30 minutes. The resulting 1 M solution of sodium 2-phenylethoxide is cooled to 60° C., 3-methoxy-α-methylstyrene oxide (1.69 g., 10.3 mmoles) added and the reaction heated 15 hours at 60° C. The reaction mixture is cooled and added to a mixture of ether and water. The ether extract is dried over magnesium sulfate and evaporated. Excess 2-phenylethanol is removed by vacuum distillation (b.p. ~65° C., 0.1 mm.). The residue is purified via column chromatography on silica gel 60 (300 g.) and eluted in 15 ml. fractions with 60% ether-pentane.

PREPARATION R

2-(3-Methoxyphenyl)propyl 2-Phenylethyl Ether

To a 0° C. solution of 2-(3-methoxyphenyl)-2-hydroxypropyl 2-phenylethyl ether (498 mg., 1.74 mmole) in pyridine (2 ml.) is added dropwise phosphorous oxychloride (477 μl., 5.22 mmole). The reaction is allowed to warm to 20° C. over a 1.5 hour period. It is then stirred for 1.5 hours at 20° C. and then added to ether (150 ml.) and 15% sodium carbonate (100 ml.). The organic phase is separated and washed with 15% sodium carbonate (3×50 ml.), dried over magnesium sulfate and evaporated to an oil. The oil is dissolved in absolute ethanol (15 ml.), 10% palladium-on-carbon (100 mg.) added and the mixture stirred under one atmosphere of hydrogen gas. When hydrogen uptake ceases the reaction is filtered through diatomaceous earth and the filtrate evaporated to an oil. The oil is purified via preparative layer chromatography on silica gel plates, eluted twice with 6:1 pentane:ether to yield the title compound.

PREPARATION S

2-(3-Hydroxyphenyl)propyl 2-Phenylethyl Ether

A mixture of 2-(3-methoxyphenyl)propyl 2-phenylethyl ether (176 mg., 0.65 mmole), pyridine (0.4 ml., 4.96 mmole) and dry pyridine hydrochloride (4 g., 34.6 mmole) is heated at 190° C. for 6 hours. The reaction mixture is cooled and added to a mixture of water (100 ml.) and ether (150 ml.). The ether extract is washed once with water (50 ml.) and, along with a second ether extract (50 ml.) of the aqueous phase, is dried over magnesium sulfate and evaporated to an oil. The oil is purified via preparative layer chromatography on silica gel plates, eluted six times with 30% ether-pentane to yield the title product.

The following compounds are prepared from appropriate alkanols by the methods of Procedures Q and R:

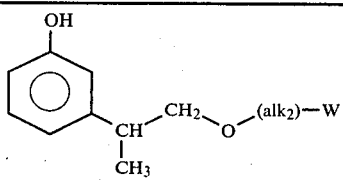

| (alk$_2$) | W |
|---|---|
| —(CH$_2$)$_7$— | H |
| —(CH$_2$)$_6$— | C$_6$H$_5$ |
| —(CH$_2$)$_5$— | H |
| —CH(CH$_3$)CH$_2$ | H |
| —CH(CH$_3$)(CH$_2$)$_5$ | H |
| —(CH$_2$)— | 4-FC$_6$H$_4$ |
| —(CH$_2$)$_2$— | 4-pyridyl |
| —(CH$_2$)$_2$— | 4-ClC$_6$H$_4$ |
| —(CH$_2$)$_2$CH(CH$_3$)(CH$_2$)$_3$— | H |
| —CH(CH$_3$)CH$_2$— | H |
| —C(CH$_3$)$_2$CH$_2$— | H |
| —(CH$_2$)$_{10}$— | H |
| —CH$_2$— | C$_6$H$_5$ |

PREPARATION T

3-Methoxy-β-methylstyrene Oxide

To a −78° C. solution of diphenylsulfonium ethylide (1.0 mole) in tetrahydrofuran (one liter) is slowly added 3-methoxybenzaldehyde (1.0 mole). The reaction mixture is stirred at −78° C. for 3 hours and then allowed to warm to room temperature. It is then added to ether-water and the ether phase separated. The ether phase is washed with water, dried (MgSO$_4$) and evaporated. Fractional distillation of the residue gives the title product.

PREPARATION U

3-(3-Hydroxyphenyl)-2-propylbutyl Ether

To a solution of sodium butoxide in butanol (0.5 liters of 1 M) is added 3-methoxy-β-methylstyrene oxide (6.33 mole). THe mixture is heated for 18 hours at 70° C. and is then cooled and added to a mixture of ether-water. The ether solution is separated, dried (MgSO$_4$) and evaporated to give the crude product 2-(3-methoxyphenyl)-3-hydroxy-2-propylbutyl ether. It is purified by column chromatography on silica gel with ether-pentane elution.

By means of the procedure of Preparation R the title product is produced.

Similarly, the following are prepared from appropriate alcohols:

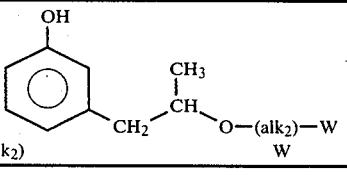

| (alk$_2$) | W |
|---|---|
| (CH$_2$)$_2$ | H |
| (CH$_2$)$_7$ | H |
| (CH$_2$)$_3$ | C$_6$H$_5$ |
| (CH$_2$)$_2$ | 4-FC$_6$H$_4$ |
| (CH$_2$)$_2$ | 4-pyridyl |

-continued

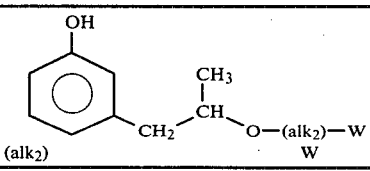

| (alk$_2$) | W |
|---|---|
| CH(CH$_3$)(CH$_2$)$_2$ | H |
| CH(C$_2$H$_5$)(CH$_2$)$_3$ | H |
| CH(CH$_3$)CH$_2$ | C$_6$H$_5$ |
| CH$_2$ | H |
| (CH$_2$)$_2$ | 4-ClC$_6$H$_4$ |

PREPARATION V

1-Bromo-3-(3-methoxyphenyl)butane

A solution of phosphorous tribromide (5.7 ml., 0.06 mole) in ether (30 ml.) is added to a solution of 3-(3-methoxyphenyl)-1-butanol (30.0 g., 0.143 mole) in ether (20 ml.) at −5° C. to −10° C. and the reaction mixture stirred at −5° C. to −10° C. for 2.5 hours. It is then warmed to room temperature and stirred for an additional 30 minutes. The mixture is poured over ice (200 g.) and the resulting mixture extracted with ether (3×50 ml.). The combined extracts are washed with 5% sodium hydroxide solution (3×50 ml.) saturated sodium chloride solution (1×50 ml.) and dried (Na$_2$SO$_4$). Removal of the ether and vacuum distillation of the residue affords the title product.

The following compounds are prepared from 3-methoxybenzaldehyde, 3-methoxyacetophenone and 3-methoxypropiophenone and the appropriate carbethoxyalkylidene triphenylphosphorane by the procedures of Preparations L, M and the above procedure.

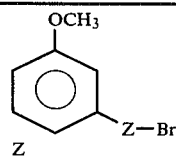

| Z |
|---|
| (CH$_2$)$_3$ |
| (CH$_2$)$_4$ |
| CH(C$_2$H$_5$)CH$_2$ |
| CH(CH$_3$)CH$_2$ |
| CH(CH$_3$)(CH$_2$)$_3$ |

PREPARATION W

1-Substituted-4-piperidones

A mixture of ethyl acrylate (3 moles) and the appropriate amine R$_6$'NH$_2$ (1 mole) in dry ethanol (200 ml.) is stirred and refluxed for 48 hours. The reaction mixture is then fractionally distilled to give the corresponding N-di-(2-carbethoxyethyl-R$_6$'-amine [R$_6$'-N-(CH$_2$—CH$_2$—COOC$_2$H$_5$)$_2$].

The disubstituted amine (1 mole) is then cyclized by treatment with metallic (bird shot) sodium (49.5 g.) in xylene (one liter) and the mixture warmed to 50° C., care being taken to exclude moisture. Additional base is added drop-wise to maintain the reaction. The reaction mixture is stirred at 50° C. for 3-4 hours following addition of the base and then cooled. Water (one liter) is cautiously added, the aqueous phase separated, extracted with ether (4×200 ml.) and then acidified with concentrated hydrochloric acid. The acid solution is saturated with potassium carbonate and the oil which separates extracted with ether. The ether solution is dried (K$_2$CO$_3$) and evaporated. The residue is refluxed with 20% HCl (2 liters) for 3-4 hours and the mixture then evaporated to dryness under reduced pressure to give the desired 1-substituted-4-piperidone.

By means of this procedure (substantially that of Beckett, et al., *J. Med. Pharm. Chem.* 1, 37-58, 1959), the following compounds are prepared.

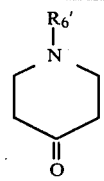

| R$_6$' |
|---|
| C$_2$H$_5$ |
| n-C$_3$H$_7$ |
| i-C$_3$H$_7$ |
| n-C$_4$H$_9$ |
| sec-C$_4$H$_9$ |
| t-C$_4$H$_9$ |
| n-C$_5$H$_{11}$ |
| n-C$_6$H$_{13}$ |
| (CH$_2$)$_3$C$_6$H$_5$ |
| (CH$_2$)$_4$C$_6$H$_5$ |
| C$_3$H$_5$ |
| furfuryl |
| tetrahydrofurfuryl |
| tetrahydrothienylmethyl |
| (CH$_2$)$_2$C$_6$H$_5$ |
| CH(CH$_3$)C$_6$H$_5$ |
| CH(CH$_3$)CH$_2$C$_6$H$_5$ |

PREPARATION X

1-R$_6$'-Substituted-Azacycloalkan-3-ones

A mixture of the appropriate N-(R$_6$'-substituted)glycine ethyl ester and the appropriate ω-halo ester BrCH$_2$(CH$_2$)$_x$CH$_2$COOC$_2$H$_5$ (1 mole) is allowed to stand at room temperature for 24 hours. It is then diluted with ether, filtered and the ethereal solution evaporated.

The ω,ω'-dicarbethoxydialkyl-R$_6$'-amines [H$_5$C$_2$OOC—CH$_2$—NR$_6$'—CH$_2$(CH$_2$)$_x$—CH$_2$COOC$_2$H$_5$] are then cyclized by heating a mixture of equimolar amounts of the di-ester and sodium ethoxide at from 120°-130° C. under conditions which allow distillation of by-product ethanol. When removal of alcohol is complete, water is added to the reaction mixture and the resulting mixture extracted with ether. The aqueous solution is then acidified with hydrochloric acid and refluxed until the solution gives no color reaction with ferric chloride. Evaporation of the solution affords the HCl salt of the 1-R$_6$'-substituted-3-pyridone. Careful neutralization with potassium carbonate gives the free ketone.

In this manner the 1-R$_6$'-substituted azacycloalkan-3-ones listed below are prepared from appropriate N-R$_6$'-glycine ethyl esters and appropriate ω-bromoalkanoic acid ethyl esters.

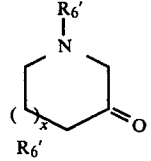

| x | R6' |
|---|---|
| 0 | cyclohexylmethyl |
| 1 | cyclopentylmethyl |
| 1 | cyclohexylmethyl |
| 2 | cyclobutylmethyl |
| 3 | cyclohexylmethyl |
| 0 | CH2C6H5 |
| 0 | CH3 |
| 0 | n-C3H7 |
| 0 | (CH2)2C6H5 |
| 0 | cyclobutylmethyl |
| 0 | cyclopropylmethyl |
| 0 | furfuryl |
| 0 | 2-tetrahydrothienylmethyl |
| 1 | CH3 |
| 1 | t-C4H9 |
| 1 | i-C6H13 |
| 1 | furfuryl |
| 1 | tetrahydrofurfuryl |
| 1 | 2-tetrahydrothienylmethyl |
| 1 | (CH2)2C6H5 |
| 1 | (CH2)4C6H5 |
| 1 | cyclobutylmethyl |
| 1 | cyclopropylmethyl |
| 2 | CH3 |
| 2 | i-C3H7 |
| 2 | n-C5H11 |
| 2 | cyclopropylmethyl |
| 2 | (CH2)3C6H5 |
| 2 | tetrahydrofurfuryl |
| 2 | CH2C6H5 |
| 3 | CH3 |
| 3 | sec-C4H9 |
| 3 | n-C6H13 |
| 3 | (CH2)3C6H5 |
| 3 | cyclopropylmethyl |
| 3 | 2-2-tetrahydrothienylmethyl |
| 3 | CH2C6H5 |
| 1 | n-C3H7 |
| 1 | i-C3H7 |
| 0 | 2-thienylmethyl(thenyl) |
| 1 | 2-thienylmethyl(thenyl) |
| 0 | CH(CH3)C6H5 |
| 2 | CH(CH3)CH2C6H5 |

The N-R6'-glycine ethyl esters not described in the art are prepared by reacting 2 moles of the appropriate amine in anhydrous ether at 0°–10° C. with one mole of ethyl bromoacetate. The mixture is stirred for 3 hours then allowed to stand overnight. The precipitate is filtered off, the ether evaporated and the residue vacuum distilled.

PREPARATION Y

Repetition of the procedure of Preparation X but using the appropriate N-(R6'-substituted)-β-alanine ethyl ester in place of the N-(R6'-substituted)-glycine ethyl ester affords compounds having the formula

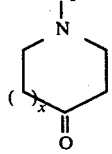

| x | R6' |
|---|---|
| 2 | CH3 |

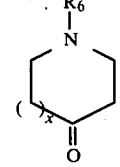

| x | R6' |
|---|---|
| 2 | n-C6H13 |
| 2 | (CH2)3C6H5 |
| 2 | cyclopropyl |
| 2 | cyclopropylmethyl |
| 2 | 2-tetrahydrothienylmethyl |
| 2 | furfuryl |
| 3 | C2H5 |
| 3 | tetrahydrofurfuryl |
| 3 | cyclopropyl |
| 3 | (CH2)4C6H5 |

PREPARATION Z

1-Benzyl-4-(3-phenylpropyl)-3-piperidone

To a 0° C. solution of 7.0 mmols. of 3-phenylpropylmagnesium bromide in 7 ml. of tetrahydrofuran is slowly added a solution of 0.95 g. (5.0 mmols.) of 1-benzyl-4-piperidone in 10 ml. of tetrahydrofuran. The resultant mixture is stirred for one hour and is then added to 250 ml. of saturated ammonium chloride-250 ml. ether. The ether phase is dried over magnesium sulfate and evaporated. The residue is purified via column chromatography on 200 g. of silica gel eluted with 50% ether-cyclohexane to yield 1-benzyl-4-(3-phenylpropyl)-piperidinol.

The thus-prepared piperidinol (6.18 g., 20 mmols.) is then added to 2 N hydrochloric acid (250 ml.) and the mixture refluxed for 6 hours. It is then evaporated under reduced pressure and the residue taken up in 500 ml. of saturated sodium bicarbonate-300 ml. of ether-100 ml. of dichloromethane. The organic phase is separated, dried (MgSO4) and evaporated to an oil which is purified by column chromatography on 400 g. of silica gel eluted with 50% ethercyclohexane to give the product 1-benzyl-4-(3-phenylpropyl)-1,2,5,6-tetrahydropyridine.

Hydroboration and subsequent oxidation of the thus-produced 1,2,5,6-tetrahydropyridine according to the procedure of Example 5 gives 1-benzyl-4-(3-phenylpropyl)-3-piperidinol.

Oxidation of the 3-piperidinol compound by the procedure of Example 6 yields the desired 1-benzyl-4-(3-phenylpropyl)-3-piperidone.

The following compounds are prepared in like manner from appropriate Grignard reagents R2MgBr and the appropriate 1-(R6'-substituted)azacycloalkan-3-one:

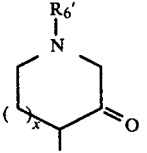

| x | R6' | R2' |
|---|---|---|
| 1 | CH3 | CH3 |
| 1 | CH3 | n-C3H7 |
| 1 | CH3 | n-C6H13 |
| 1 | n-C3H7 | n-C5H11 |

-continued

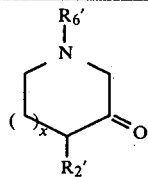

| x | R6' | R2' |
|---|---|---|
| 1 | i-C3H7 | C2H5 |
| 1 | t-C4H9 | n-C4H9 |
| 1 | i-C6H13 | CH3 |
| 1 | THF | CH3 |
| 1 | THF | n-C6H13 |
| 1 | CH2C6H5 | CH3 |
| 1 | CH2C6H5 | n-C3H7 |
| 1 | (CH2)4C6H5 | i-C3H7 |
| 1 | (CH2)2C6H5 | CH3 |
| 1 | CH2C6H5 | (CH2)3C6H5 |
| 1 | C3H5 | CH3 |
| 1 | C3H5 | n-C4H9 |
| 1 | C3H5CH2 | CH3 |
| 1 | C3H5CH2 | n-C6H12 |
| 1 | C3H5CH2 | (CH2)2C6H5 |
| 1 | C3H5 | C6H5 |
| 1 | CH3 | C6H5 |
| 1 | t-C4H9 | C6H5 |
| 1 | furfuryl | CH3 |
| 1 | furfuryl | (CH2)4C6H5 |
| 1 | furfuryl | n-C5H11 |
| 1 | THTM | CH3 |
| 1 | THTM | sec-C4H9 |
| 1 | THTM | (CH2)3C6H5 |
| 1 | THTM | (CH2)4C6H5 |
| 1 | THF | C6H5 |
| 0 | CH3 | CH3 |
| 0 | CH3 | i-C3H7 |
| 0 | n-C3H7 | i-C6H13 |
| 0 | CH3 | C6H5 |
| 0 | n-C3H7 | (CH2)3C6H5 |
| 0 | (CH2)2C6H5 | C2H5 |
| 0 | C3H5 | n-C3H7 |
| 0 | C3H5 | (CH2)2C6H5 |
| 0 | C3H5CH2 | CH3 |
| 0 | furfuryl | C2H5 |
| 0 | THTM | CH3 |
| 0 | THTM | C6H5 |
| 2 | CH3 | CH3 |
| 2 | CH3 | n-C5H11 |
| 2 | i-C3H7 | (CH2)3C6H5 |
| 2 | n-C5H11 | CH3 |
| 2 | CH2C6H5 | CH3 |
| 2 | CH2C6H5 | n-C4H9 |
| 2 | (CH2)4C6H5 | CH3 |
| 2 | C3H5 | C2H5 |
| 2 | C3H5 | (CH2)3C6H5 |
| 2 | C3H5 | C6H5 |
| 2 | (CH2)3C6H5 | CH3 |
| 2 | THF | CH3 |
| 2 | THF | C6H5 |
| 0 | CH2C6H5 | CH3 |
| 0 | CH2C6H5 | n-C6H13 |
| 0 | CH2C6H5 | C6H5 |
| 3 | CH3 | CH3 |
| 3 | CH3 | i-C3H7 |
| 3 | CH3 | n-C6H13 |
| 3 | CH3 | (CH2)3C6H5 |
| 3 | sec-C4H9 | CH3 |
| 3 | sec-C4H9 | C6H5 |
| 3 | sec-C4H9 | i-C3H7 |
| 3 | n-C6H13 | CH3 |
| 3 | n-C6H13 | n-C5H11 |
| 3 | C3H5CH2 | CH3 |
| 3 | C3H5CH2 | n-C4H9 |
| 3 | C3H5CH2 | (CH2)2C6H5 |
| 3 | C3H5CH2 | C6H5 |
| 3 | THTM | C6H5 |
| 3 | THTM | (CH2)3C6H5 |
| 3 | CH2C6H5 | CH3 |
| 3 | CH2C6H5 | n-C4H9 |

-continued

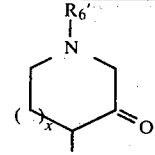

| x | R6' | R2' |
|---|---|---|
| 3 | (CH2)4C6H5 | CH3 |
| 3 | THF | CH3 |
| 3 | C3H5 | i-C3H7 |
| 2 | C3H5CH2 | n-C3H7 |
| 2 | C3H5CH2 | (CH2)3C6H5 |
| 2 | n-C6H13 | CH3 |

THF = tetrahydrofurfuryl
THTM = 2-tetrahydrothienylmethyl

What is claimed is:
1. A compound having the formula

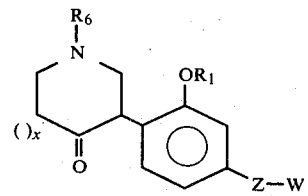

wherein $R_1$ is selected from the group consisting of hydrogen, benzyl and alkanoyl having from one to five carbon atoms;
$R_6$ is selected from the group consisting of hydrogen, alkenyl having from two to six carbon atoms, alkynyl having from two to six carbon atoms and $R_6'$ wherein $R_6'$ is selected from the group consisting of alkyl having from one to six carbon atoms, phenylalkyl having from one to four carbon atoms in the alkyl group and cycloalkylmethyl having from three to six carbon atoms in the alkyl group;
x is 0 or an integer from 1 to 3;
Z is selected from the group consisting of
(a) alkylene having from one to thirteen carbon atoms;
(b) —(alk$_1$)$_m$—O—(alk$_2$)$_n$— wherein each of (alk$_1$) and (alk$_2$) is alkylene having from one to thirteen carbon atoms, with the proviso that the summation of carbon atoms in (alk$_1$) plus (alk$_2$) is not greater than thirteen; each of m and n is 0 or 1;
and W is selected from the group consisting of pyridyl and

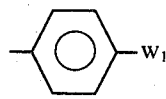

wherein $W_1$ is selected from the group consisting of hydrogen, fluoro and chloro; or a pharmaceutically acceptable acid addition salt thereof.
2. A compound according to claim 1 wherein each of $R_1$ and $R_6$ is benzyl.
3. A compound according to claim 2 wherein Z is alkylene and W is phenyl.
4. A compound according to claim 2 wherein Z is (alk$_1$)$_m$—O—(alk$_2$)$_n$ wherein m is 0 and n is 1 and W is

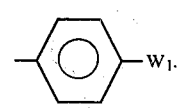

5. The compound according to claim 4 wherein Z is —OCH(CH$_3$)(CH$_2$)$_3$, W is phenyl and x is 1.

* * * * *